United States Patent
Manesis et al.

(10) Patent No.: US 11,692,075 B2
(45) Date of Patent: Jul. 4, 2023

(54) BIOCOMPATIBLE POROUS MATERIALS AND METHODS OF MANUFACTURE AND USE

(71) Applicant: Poragen LLC, San Diego, CA (US)

(72) Inventors: Nicholas J. Manesis, Escondido, CA (US); Dylan B. Hollrigel, San Clemente, CA (US)

(73) Assignee: Poragen LLC, San Diego, CA (US)

( * ) Notice: Subject to any disclaimer, the term of this patent is extended or adjusted under 35 U.S.C. 154(b) by 0 days.

(21) Appl. No.: 17/451,360

(22) Filed: Oct. 19, 2021

(65) Prior Publication Data

US 2022/0033611 A1 Feb. 3, 2022

Related U.S. Application Data

(63) Continuation of application No. 17/214,702, filed on Mar. 26, 2021, now Pat. No. 11,149,127.

(60) Provisional application No. 63/001,049, filed on Mar. 27, 2020.

(51) Int. Cl.
*C08J 9/36* (2006.01)
*C08J 7/04* (2020.01)
*C08J 7/056* (2020.01)

(52) U.S. Cl.
CPC .............. *C08J 9/365* (2013.01); *C08J 7/042* (2013.01); *C08J 7/056* (2020.01); *C08J 2205/044* (2013.01); *C08J 2205/05* (2013.01); *C08J 2375/04* (2013.01); *C08J 2433/14* (2013.01); *C08J 2483/04* (2013.01)

(58) Field of Classification Search
CPC ........ A61L 15/24; A61L 15/26; A61L 15/425; A61L 27/18; A61L 27/34; A61L 27/52; A61L 27/56; A61L 31/06; A61L 31/10; A61L 31/145; A61L 31/146; A61L 2420/08; C08J 7/042; C08J 7/056; C08J 9/365; C08J 9/405; C08J 9/42; C08J 2205/044; C08J 2205/05; C08J 2207/10; C08J 2375/04; C08J 2405/08; C08J 2427/16; C08J 2433/14; C08J 2439/06; C08J 2483/04

See application file for complete search history.

(56) References Cited

U.S. PATENT DOCUMENTS

| | | | |
|---|---|---|---|
| 3,544,489 A | 12/1970 | Dowbenko et al. | |
| 4,595,610 A | 6/1986 | Fey et al. | |
| 4,889,744 A | 12/1989 | Quaid | |
| 5,153,231 A | 10/1992 | Bouquet et al. | |
| 5,872,190 A | 2/1999 | Gutowski et al. | |
| 7,972,628 B2 | 7/2011 | Ratner et al. | |
| 8,679,570 B2 * | 3/2014 | Goraltchouk | C08J 9/365 623/7 |
| 11,149,127 B1 | 10/2021 | Manesis et al. | |
| 2003/0065377 A1 * | 4/2003 | Davila | A61L 31/10 623/1.42 |
| 2005/0143480 A1 | 6/2005 | Hirayama et al. | |
| 2007/0244379 A1 | 10/2007 | Boock et al. | |
| 2008/0114276 A1 | 5/2008 | Janusson et al. | |
| 2011/0196488 A1 | 8/2011 | Goraltchouk et al. | |
| 2012/0077891 A1 | 3/2012 | Liu et al. | |
| 2012/0101574 A1 | 4/2012 | Goraltchouk et al. | |
| 2012/0239161 A1 | 9/2012 | Datta et al. | |
| 2013/0023987 A1 | 1/2013 | Liu et al. | |
| 2013/0032962 A1 | 2/2013 | Liu et al. | |
| 2014/0275864 A1 | 9/2014 | Drury | |
| 2015/0028510 A1 | 1/2015 | Liu et al. | |
| 2015/0245899 A1 * | 9/2015 | Lyngstadaas | A61L 27/306 427/2.26 |
| 2016/0032042 A1 | 2/2016 | Burdeniuc et al. | |

FOREIGN PATENT DOCUMENTS

WO WO02/22339 A1 3/2002

OTHER PUBLICATIONS

Oh et al.; Hydrophilization of synthetic biodegradable polymer scaffolds for improved cell/tissue compatibility; Biomedical materials; 8(1); 014101; Jan. 25, 2013.

* cited by examiner

*Primary Examiner* — John M Cooney
(74) *Attorney, Agent, or Firm* — Shay Glenn LLP; Thomas M. Zlogar

(57) ABSTRACT

Methods and materials used for production of constructs having a porous open or semi-open celled structure. Constructs may include a porous matrix as a base and a biocompatible conformal coating thereon.

19 Claims, 7 Drawing Sheets

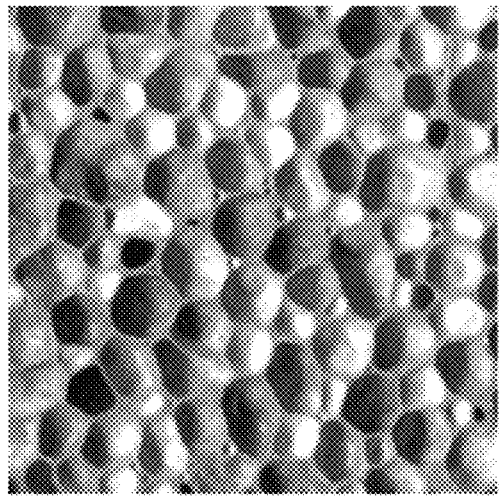
Figure 3C Fully Closed Cell Material
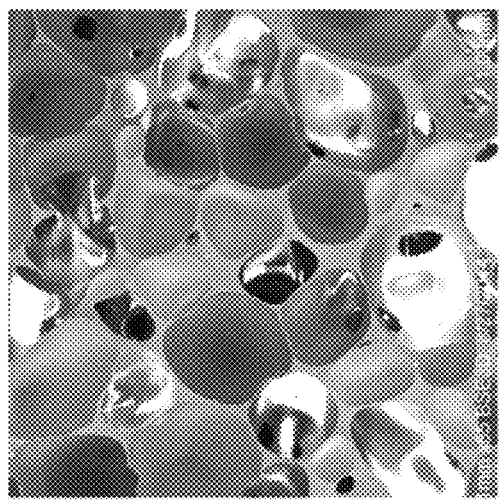
Figure 3B Semi-Open Cell Material
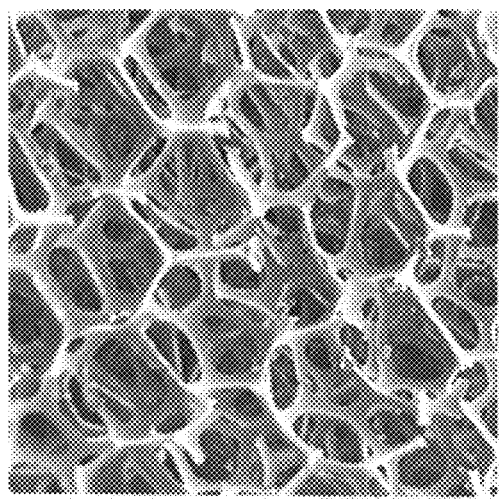
Figure 3A Fully Open Cell Material

BIOCOMPATIBLE POROUS MATERIALS AND METHODS OF MANUFACTURE AND USE

CROSS-REFERENCE TO RELATED APPLICATIONS

This application is a continuation of U.S. application Ser. No. 17/214,702, filed Mar. 26, 2021, which claims the benefit of U.S. Provisional Application No. 63/001,049, filed Mar. 27, 2020, the disclosures of each are fully incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Foams are used in a variety of industrial and consumer applications ranging from cushioning in car seats to vibration reduction and sound insulation. Foams range in mechanical properties from rigid to flexible, and in microstructure from fully open celled to fully closed cell, where the pores are all fully interconnected to at least greater than 2 other pores and where the pores are fully isolated from each other, respectively. Flexible open celled foams are predominantly produced out of polyurethane, where a reaction of an isocyanate and a polyol in the presence of, optionally one or more of, water, a crosslinker, prepolymer, catalyst, filler, or a blowing agent control the foams mechanical, chemical, and structural properties. However, the structural properties of open celled polyurethane foams is generally limited to 20-140 pores per inch (ppi) with individual pore sizes ranging generally from 25 to 2500 um. Similarly, the chemical properties are limited to the properties of the material that the construct is manufactured from. As such, ester based polyols are susceptible to hydrolytic attack and perform poorly in some acid or base contacting applications. Similarly, as an example, thermal stability is limited to the thermal stability of the polyurethane chain (generally not exceeding 150° C. operating temperature). Finally, mechanical properties are limited to the combination of the microstructure and the polymer chain, and therefore in the case of polyurethane foams to the mechanical properties of the polyurethane that is used to make the material.

Due to these limitations, polyurethane foams are unable to perform in many applications where their biological, chemical, structural, or mechanical properties are not suitable. As such, constructs with similar microstructure (or one that is variable outside the range available for current polyurethane foams) are desired from other, non-polyurethane, materials. For this reason, non-polyurethane foams have been produced including open celled polyolefin foams (e.g., WIPO Patent Application WO/2002/022339) and silicone foams (e.g., U.S. Pat. No. 5,153,231). However, the microstructure of these materials is highly limited in its variety of pore sizes, interconnections per pore, structure of the outer skin, porosity, size of interconnections, and size of supporting struts. Most importantly, however, the properties of these materials are substantially lower than what would be expected for the raw material itself. Silicones, for example, can attain elongation at break of over 1200%, while open celled polyurethane foams have a difficulty of attaining an elongation at break of 40-100%.

Methods are needed to produce microstructures that have an open or semi-open celled, interconnected network, with a controllable pore size, porosity, interconnectivity, number of interconnections per pore, interconnection diameter, and strut size, and possess mechanical and chemical properties similar to that of the base material.

It is therefore desired to create composite foam structures, of a range of polymers and composites comprising the bulk that does not compromise mechanical, chemical, or microstructural properties of the foam.

Structures that include a foam may find non-limiting uses in medical applications, such as those that include contact with tissue. In these medical applications, the structure may need to be biocompatible, low-density, and have a relatively high porosity. Additionally, the structure may benefit from one or more physical characteristics not attainable with the underlying foam material alone. As such, the structure may benefit from being modified in one or more ways to impart one or more desired physical characteristics.

SUMMARY OF THE DISCLOSURE

The disclosure herein is related to the field of open celled and semi-open celled porous materials.

Porous structures and structures containing voids are used in a variety of medical applications. For instance, felts and woven fabrics are used as buttress structures for suturing and anastomosis support, other fabrics are used in cardiac applications, for instance the use of cardiac meshes and felts is highly prevalent. The use of meshes is also abundant in gynecology and general surgery to support hernias, fixation of tissue, general tissue bulking, and mechanical support. Fibrous materials, specifically woven fabrics are also used as support slings in breast implant applications, especially during reconstructive surgery. Porous, non-fibrous, and fibrous structures have also been used in tissue engineering applications, as well as bone grafting, reconstruction, and augmentation. In general, the structures may be divided into two general subsets—1) porous, open celled or semi-open celled structures, and 2) fibrous structures, containing felts, non-wovens, knit fabrics, woven fabrics or the like. Open celled or semi-open celled structures have predominantly been made by a lost-porogen approach, gas foaming, or emulsification with subsequent solidification. Fabrics, wovens, non-wovens, and felts are made by standard textile processing techniques. In general, open or semi-open celled structures have poor mechanical properties, limited interconnectivity, porosity, or interconnection diameters. Control over the microstructure of such materials is poor, as such, applications are generally limited. Felts, and non-wovens, have a tissue-like architecture, and are generally substantially interconnected, containing a significant amount of porosity, however, the mechanical properties of non-wovens are generally poor with fibers being readily removable, structure easily lost, and elongation at break, for the most part, very low. Woven or knitted fabrics have thick, non-tissue like, fibers and fiber complexes, are typically limited to one layer creating an environment prone to foreign body capsule formation in the plane of the fabric. The limited porosity and interconnectivity of such structures does not allow for sufficient tissue disorganization and biocompatibility into the surrounding tissue for maximum mechanical- and biocompatibility. The limited porosity and interconnectivity of such structures also minimizes use of such devices in topical applications desiring the covering of a wound, exudate removal, mechanical contact prevention, and the like. Polyurethane foams, for example, have a microstructure that provides sufficient porosity and interconnectivity for good tissue ingrowth, exudate absorption and removal, barrier to mechanical contact, exudate absorption, and sufficient mechanical strength. Furthermore, the mechanical properties of polyurethane are highly compatible with many surrounding tissues. While control over the microstructure is somewhat limited, the existing microstructure and mechanical properties afford good tissue biocompatibility, mechanical compatibility, and prevent the formation of a foreign body response in its classical sense, allowing nutrient transmission throughout the implant, cellular mobility, prevent an increase in the risk of infection or isolation by the body, and allow for an optimal environment to form a natural tissue architecture. Polyurethanes are, however, highly limited in their biomedical applications as foams due to the undesirable biodegradation that the polymer backbone undergoes in the presence of body fluids, tissues, and cells, and the release of potentially toxic or carcinogenic by-products. Biodegradation of polyurethane can be initiated after a short exposure time to biological tissue and can last several months to one year or more, thereby, leading to complete degradation of the polyurethane device.

An open- or semi-open celled structure is desirable in a variety of medical applications either as a standalone device or as a component in an assembly or finished device. Chemistry of the structure may afford stability in-situ or have controlled biodegradation, and preferably by modifiable with biological agents, and optionally bioactive. The structure should have a uniquely defined set of physical and chemical properties, as well as a microstructure that can create an optimal environment for tissue contact and tissue integration if desired. Finally, the open celled structure must be biocompatible and should be tailorable in its microstructure, physical, chemical, and biological properties to suit specific individual medical applications.

As used herein, open celled or open cell may also be referred to as open pore, and vice versa.

One non-limiting aspect of the disclosure relates to open or semi-open celled constructs, which optionally may find use in medical applications. The constructs may be biocompatible for medical uses while at the same time being low density, highly porous, and at least 50% porosity (% open cell), and preferably more than 75% porosity, or more. The constructs may optionally be manufactured in a way that imparts greater compliance to the construct without the manufacturing step. Additionally or alternatively, the constructs may possess wettability, which may be imparted during manufacture of the construct. One non-limiting aspect of the disclosure relates to methods of manufacturing open or semi-open celled constructs, wherein the constructs may optionally find use in medical applications. The manufactured constructs, if used in medical applications, may be biocompatible while at the same time being low-density and relatively highly porous. The manufacturing process may optionally impart greater compliance to the construct, and additionally or alternatively, the manufacturing process may impart wettability to the final construct.

As used herein, % porosity of the construct refers to % of the construct that is open cell or open pore, or cells (pores) that are interconnected to other pores rather than being blocked from adjacent pores. Additionally, the phrase highly porous herein refers to constructs that have high porosity, such as from 50-98% porosity, such as 80-98% porosity.

In some examples, the disclosure provides processes for making porous open celled constructs from polyurethane polymers and foams as a matrix or template material.

In some aspects, the disclosure includes methods of forming or manufacturing porous structures by use of a porous, open or semi-open celled template structure which remains in place and becomes part of the final composite porous structure. The manufactured structure may be referred to herein as a construct or final (or finished) construct.

In some examples, the final construct includes a biocompatible layer or coating, such as a silicone layer or coating. The biocompatible layer may be a conformal silicone layer and may be disposed on a porous polyurethane matrix. The biocompatible layer may impart biocompatibility to the final construct, which may be beneficial or essential in some medical applications. The final construct may be biocompatible due to a biocompatible layer, but may still be highly porous. A biocompatible layer may be sufficiently thin so as not to reduce the porosity of the final construct in a meaningful way.

Optionally, after a biocompatible layer or coating (e.g., silicone) is created or formed on a porous template structure, one or more additional properties may be imparted to the biocompatible construct. For example only, some uses of the construct (e.g., medical) may benefit if the construct has a compliance or softness not attained after adding the biocompatible layer. Added or increased compliance may help the construct conform better to some tissue or anatomy. In some examples herein, the compliance of the construct may be increased by one or more manufacturing steps. For example only, the construct may be exposed to an agent that increase the compliance, such as DMSO, which was an unexpected result. Additionally or alternatively, wettability may be imparted to the construct, such as by adding a hydrophilic layer (e.g., a hydrogel) on the conformal biocompatible structure.

In some alternative aspects, the disclosure includes methods of forming resulting porous structures by use of a porous, open or semi-open celled template structure that is dissolved by contact with chemical agent or agents resulting in a template-free porous construct.

In some aspects, methods of manufacture herein may include providing porous, open celled or semi-open celled structures, coating such structures or impregnating such structures with a material, removing excess material to generate a desired composite structure, solidifying, curing, drying, and/or polymerization of the coating material, and optionally one or more post processing steps thereafter such as sterilization, purification, washing, or other steps. The steps performed and/or their order during manufacture may be based on the specific application of use of the manufactured structure.

In some aspects the disclosure herein describes the constructs that are manufactured, in general, porous structures, including interconnected or semi-interconnected pores, with strut sizes surrounding those pores, void sizes inside the struts, average interconnectivity of the pores, pore sizes, and interconnection diameters. These parameters may be within certain ranges depending on the steps in the method of manufacture. Particular applications of use may dictate, require, or benefit from one or more of these construct parameters.

Additionally, in some aspects, the disclosure herein describes materials that comprise the final construct structure including the base materials, additives that are used to create a polymer-polymer blend, polymer-ceramic, or polymer-metal composite, and coatings of the structure.

One aspect of this disclosure is a biocompatible open or semi-open celled material for medical applications.

In this aspect, the material may comprise an open or semi-open celled construct. The construct may include a plurality of struts, which optionally may have a thickness from 30 microns to 95 microns. The plurality of construct struts may include a matrix template (e.g., comprising or consisting of a polyurethane matrix) and a conformal biocompatible layer (e.g., silicone) on the matrix template. The conformal biocompatible layer optionally and preferably has a thickness from 1 micron to 20 microns (which may alternatively be up to 50 microns, depending on the need). The construct struts may also optionally (not necessarily) include a hydrophilic coating on the conformal biocompatible layer, which may impart wettability to the final construct. Optional hydrophilic coatings may have a thickness less than 10 microns, such as 5 microns or less. The plurality of struts define a plurality of pores (open space), and the final construct may have 80-99% porosity, such as 85%-98% porosity, such as 90%-99% porosity. The plurality of pores optionally have a diameter from 200 to 900 microns. The plurality of pores optionally have an interconnection diameter from 5-2200 microns.

In this aspect, an optional hydrophilic coating may be covalently bonded to the conformal biocompatible layer and may be covalently bonded to itself.

In this aspect, an optional hydrophilic coating may comprise at least one of PEGA, HEA, or HEMA.

In this aspect, the biocompatible (e.g., silicone) coating may optionally have a thickness from 1 micron to 15 microns, such as from 5 microns to 15 microns, such as 5 to 10 microns.

In this aspect, the construct, in an image taken of a top or a bottom of the construct, may have an open area %, defined as open space between the plurality of struts, from 20-35%.

In this aspect the construct may have a density of 0.01 g/cc to 0.2 g/cc.

In this aspect, the construct may have a measured SAG from 45 mm to 60 mm, which may be at least partially due to a compliance enhancing step during the manufacture of the construct.

In this aspect, an optional hydrophilic coating may have a water content from 50% to 95%, such as from 60% to 95%, such as from 70% to 90%, optionally about 70%, about 75%, about 80% or about 85%.

One aspect of the disclosure is an open or semi-open celled construct that includes a plurality of struts, wherein the plurality of struts include a polyurethane matrix and a conformal silicone coating on the polyurethane template. The plurality of struts may have a thickness from 30 microns to 95 microns and the conformal silicone coating may have a thickness from 1 micron to 20 microns. The plurality of struts define a plurality of pores, and the construct may have 80-98% porosity. The plurality of pores may have a diameter from 200 to 600 microns. The plurality of pores may have an interconnection diameter from 5-2200 microns.

In this aspect, the silicone coating may have a thickness from 1 micron to 15 microns, such as from 1 micron to 10 microns, or from 5 microns to 15 microns, for example.

In this aspect, the construct may have a density of 0.01 g/cc to 0.2 g/cc.

In this aspect, the construct may have a measured SAG from 45 mm to 60 mm.

This aspect may include any other suitable construct feature claimed, described and/or illustrated herein.

One aspect of this disclosure is a method of making a biocompatible open or semi-open celled construct, optionally for medical applications.

This aspect may include submerging an open or semi-open celled foam matrix or template (e.g., a polyurethane matrix) into a dispersion (e.g., a silicone dispersion) to expose the foam matrix to dispersion, the foam template comprising a plurality of template struts that define a plurality of template pores. The method may also include allowing the dispersion to pass into the plurality of template pores. The method may include removing at least some of the dispersion from the plurality of template pores. The method may further include curing silicone to form a conformal silicone coating on the plurality of template struts. The method may further include, at a time subsequent to the curing step, forming a hydrophilic layer on the conformal coating which may impart wettability, wherein forming a hydrophilic layer on the conformal coating creates a construct including a plurality of construct struts that define a plurality of construct pores. The plurality of construct struts may have a thickness from 30 microns to 90 microns. The conformal silicone coating may have a thickness from 1 micron to 20 microns (alternatively up to 50 microns). The construct may have 80-98% porosity, optionally 85-98% porosity, optionally 95%-98% porosity.

In this aspect, the dispersion may be at most 35% silicone, which may contribute to being able to form a relatively thin conformal biocompatible layer on the matrix template.

In this aspect, the construct, in an image of a top or a bottom of the construct, has an open area %, defined as open space between the plurality of struts, and wherein the matrix in the absence of the conformal, in an image of a top or a bottom of the polyurethane matrix, has an open area %, defined as open space between the plurality of matrix struts, and optionally wherein the difference between the construct open area % and the matrix open area % is less than 10%, optionally wherein the difference between the construct open area % and the matrix open area % is less than 5%.

In this aspect, the method may further comprise, at a time subsequent to curing the optionally biocompatible silicone conformal layer, performing an extraction to remove uncured silicone, which may also remove a minimal portion of the polyurethane foam template.

In this aspect, removing at least some of a silicone dispersion from the plurality of template pores may include spinning a polyurethane foam template to remove at least some of the silicone dispersion.

This method may further comprise repeating the submerging, allowing, removing, and curing steps. The repeating may include repeating the submerging, allowing, removing, and curing steps from 1-10 times, such as from 1-5 times, or from 1-3 times.

In this aspect, the method may further include, subsequent in time to the curing step, increasing the compliance of the coated template struts. Increasing the compliance of the plurality of construct struts may comprise exposing the plurality of coated template struts to DMSO, such as exposing the plurality of coated template struts to DMSO for at least 30 minutes. The method further include performing an extraction step to extract the DMSO.

In this aspect, the optional step of forming a hydrophilic layer on the conformal layer may comprise forming a hydrophilic layer that has a thickness of less than 5 microns. Prior to optionally forming the hydrophilic layer, the method may include corona treating the conformal silicone coating and exposing the corona treated conformal silicone coating to a coupling agent, such as a silane coupling agent. Any of the hydrophilic coatings herein may include one or more layers of hydrophilic material.

This aspect may further include any other suitable method step described or claimed herein.

One aspect of the disclosure is a method of making a biocompatible open or semi-open celled construct, optionally for medical applications. The method may include exposing an open or semi-open celled foam matrix or template (e.g., polyurethane) to a dispersion (e.g., silicone dispersion), the foam template comprising a plurality of template struts that define a plurality of template pores. The method may include allowing silicone dispersion to pass into the plurality of template pores, and removing at least some of the optional silicone dispersion from the plurality of template pores. The method may include curing silicone to form a plurality of construct struts that comprise a conformal silicone coating on the plurality of template struts, the plurality of construct struts defining a plurality of construct pores. The method may optionally include increasing the compliance of the plurality of construct struts relative to a compliance subsequent the curing step. Increasing the compliance of the plurality of construct struts may include exposing the plurality of construct struts to a compliance enhancing agent. Exposing the plurality of construct struts to a compliance enhancing agent may include exposing the plurality of construct struts to DMSO, optionally for at least 30 minutes, and the method may further include performing an extraction step to extract at least some of the DMSO.

In this aspect, the curing step may comprise curing a silicone to form a plurality of construct struts that comprise a conformal silicone coating that has a thickness from 1 micron to 20 microns. A curing step may comprise curing a silicone to form a plurality of construct struts that have a thickness from 30 microns to 90 microns. A final construct may have 80-98% porosity, such as from 90%-98% porosity.

In this aspect, the method may further comprise repeating the submerging, allowing, removing, and curing steps, optionally repeating the submerging, allowing, removing, and curing steps from 1-10 times, optionally from 1-5 times (e.g., from 1-3 times).

In this aspect the construct may have a density of 0.01 g/cc to 0.2 g/cc.

In this aspect the construct may have a measured SAG from 45 mm to 60 mm.

One aspect of the disclosure is a biocompatible open or semi-open celled construct, optionally for medical applications. The construct may be any of the constructs described or claimed herein. The construct, in an image of a top or a bottom of the construct, may have an open area %, defined as open space between the plurality of struts, from 20-35%. Alternatively or additionally, the construct, in an image taken of a cross-section that is orthogonal to a top and a bottom of the construct, may have an open area %, defined as open space between the plurality of struts, from 20-35%.

The construct may include a plurality of struts that include a base matrix or template (e.g., polyurethane) and a conformal biocompatible coating (silicone) on the base matrix. The plurality of struts may have a thickness from 30 microns to 90 microns and the conformal silicone coating may have a thickness from 1 micron to 20 microns. The plurality of struts define a plurality of pores, and the construct may have 80-98% porosity, such as 90%-98% porosity. The % open area may optionally be 25-30%.

In this aspect, the base matrix alone (e.g., polyurethane matrix), without the conformal coating (e.g., silicone), may have an open area % from 25-35%. The matrix alone, without the conformal coating, may have an % open area of 30%, for example.

In this aspect, the construct may have a density of 0.01 g/cc to 0.2 g/cc.

In this aspect, the construct may have a measured SAG from 45 mm to 60 mm.

In this aspect, the construct may further comprise a hydrophilic coating on a conformal silicone layer that may impart wettability to the construct, wherein a hydrophilic coating may optionally have a thickness of 5 microns or less.

This aspect may include any other suitable feature described or claimed herein.

One aspect of the disclosure is a biocompatible open or semi-open celled construct, optionally for medical applications. The construct may be any of the constructs herein (e.g., including a polyurethane matrix with a conformal silicone coating thereon). The construct, in an image of a top or a bottom of the construct, has an open area %, defined as open space between the plurality of struts, and the matrix or template (e.g., polyurethane) in the absence of a conformal coating, in an image along a top or a bottom of the matrix, has an open area %, defined as open space between the plurality of matrix struts, and wherein the difference between the construct open area % and the matrix open area % is less than 10%. The construct includes a plurality of struts that define a plurality of pores. The struts may include a base matrix or template (e.g., polyurethane) and a conformal coating (e.g., silicone) on the template. The plurality of struts may optionally have a thickness from 30 microns to 90 microns, and the conformal optionally silicone coating may optionally have a thickness from 1 micron to 20 microns. The plurality of struts may define a plurality of pores, wherein the construct may optionally be 80-98% porosity, such as 90% to 98% porosity.

In this aspect, the difference between the construct open area % and the matrix open area % may be less than 5%.

In this aspect, the construct may further comprise a hydrophilic coating on the conformal optionally silicone layer to impart wettability to the construct, wherein the hydrophilic coating may have a thickness less than 5 microns.

BRIEF DESCRIPTION OF THE DRAWINGS

FIGS. 3A, 3B and 3C illustrate a scanning electron micrograph image of celled materials.

DETAILED DESCRIPTION

Figure 1:
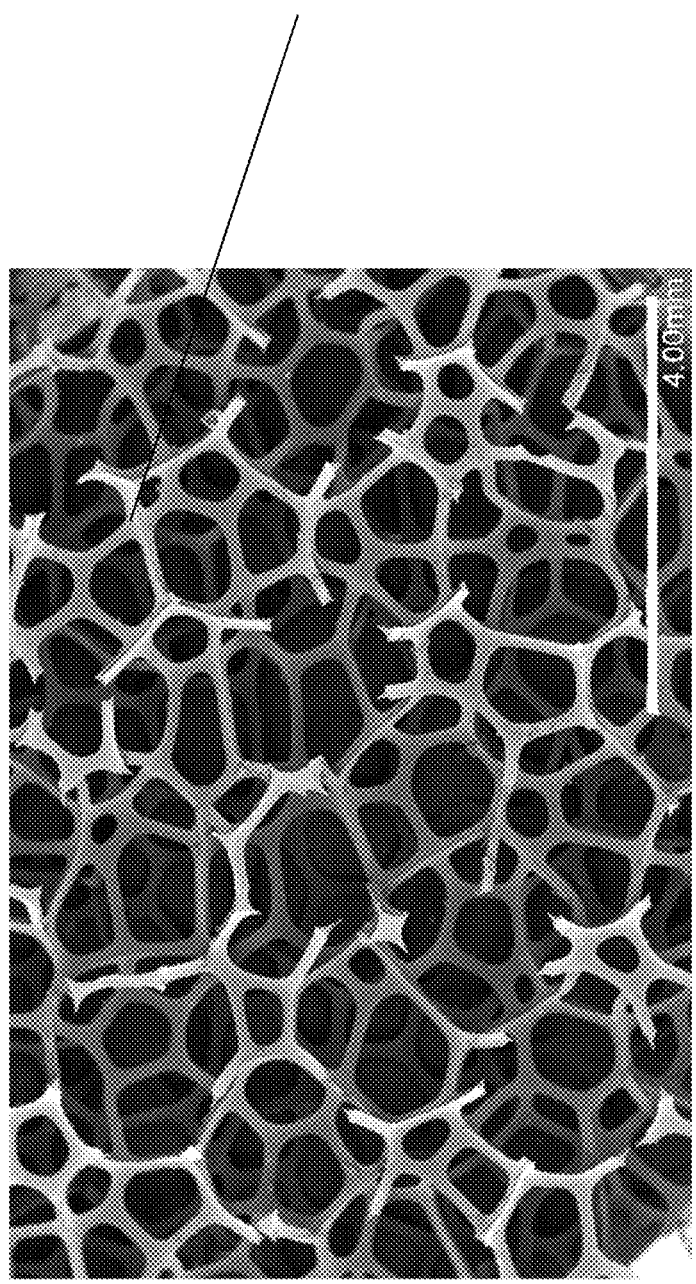
FIG. 1 illustrates a scanning electron micrograph image of a commercial open cell polyurethane foam.

The disclosure herein is related to the field of open celled and semi-open celled porous materials. A non-limiting aspect of the disclosure is open or semi-open celled constructs, which optionally may find use in medical applications. The constructs may be biocompatible for medical uses while at the same time are low-density, relatively highly porous (i.e., at least 50% porosity, and preferably at least 75% porosity, or more). The constructs may optionally be manufactured in a way that enhances the compliance or softness of the construct compared to manufacturing procedures that don't include a compliance enhancing step. The constructs may optionally be manufactured with a step or procedure that enhances the smoothness of the construct compared to manufacturing processes that do not include a smoothness enhancing step. In some examples, a single exposure step may be performed that results in an enhancement to the compliance as well as an increase in the smoothness of the final construct. Additionally or alternatively, the constructs may possess wettability, which may be imparted during manufacture of the construct. A non-limiting aspect of the disclosure relates to methods of manufacturing open or semi-open celled constructs, wherein the constructs may optionally find use in medical applications. The manufactured constructs, if used in medical applications, may be biocompatible while at the same time being low-density and relatively highly porous (i.e., at least 75% porosity, and optionally at least 80% porosity, and optionally at least 90% porosity, and optionally at least 95% porosity). The manufacturing process may optionally impart greater compliance/softness and/or softness (e.g., to decrease friction when in use) to the construct, and additionally or alternatively, the manufacturing process may impart wettability to the final construct.

One aspect of this disclosure is related to constructs with a template matrix (e.g., polyurethane) with a conformal biocompatible coating or layer thereon that makes the constructs biocompatible, yet are still highly porous and low density. Highly porous or high porosity refers generally herein to having a high percentage of open cell pores that are not blocked, with a low-density construct of struts that define the pores or open spaces. Some uses, such as medical applications, may greatly benefit from a biocompatible construct that is highly porous and low density. For example, biocompatible highly porous (high porosity), low density constructs may provide for excellent air and liquid flow therethrough. It may be highly beneficial to allow air flow through the porous material to expose the tissue to oxygen. It may be highly beneficial to allow liquid flow through the porous material in wound healing applications and uses. Additionally, the highly porous material may promote excellent tissue contact while avoiding or minimizing inflammatory issues. Additionally, the highly porous material may allow or provide for excellent tissue integration. The biocompatibility may allow the construct to be used in applications over a long period time, for example. While some relatively short term uses may include tissue contact over 3-30 days for example (or shorter), longer term applications may allow the constructs to be used in tissue contact applications for more than 30 days, such as up to 10+ years.

Depending on the application, it may thus be highly beneficial to be able to add a conformal biocompatible layer to highly porous matrix without sacrificing the highly porous nature of the construct.

In some instances, maintaining a highly porous biocompatible construct includes providing a relatively very thin conformal layer of biocompatible material on the already highly porous matrix template so as to prevent the added biocompatible material from blocking the pores and providing a high porosity construct. Exemplary method of manufacturing steps that can help provide the coating without sacrificing the highly porous nature of the final construct are described in more detail below.

In some exemplary embodiments, open or semi-open celled constructs herein may include a biocompatible layer or coating that is from 1 micron to 50 microns, such as from 2 microns to 25 microns, and in some cases is from 2 microns to 15 microns, such as from 2 microns to 10 microns. In some instances, the coating may be 5 microns or less, such as from 1-5 microns. In any of these examples, the final coating may be applied or created in a plurality of steps, each of which adds a layer or coating, wherein the final coating or layer comprises the plurality of sequentially formed layers that together define the biocompatible coating or layer.

An exemplary way to help characterize the amount of biocompatible material that is added to the base template matrix is how much the pore size is reduced after the addition of the biocompatible coating. Adding a conformal coating without a meaningful reduction is pore size helps maintain and create a highly porous final construct as described herein. The construct may be characterized in this manner by image analysis, such as digital microscopy image analysis. For example, the decrease in pore size after adding the biocompatible layer can be quantified by comparing, in two dimensions (e.g., an image), a percentage of the 2D area that is open (open area) between the struts of the porous structure before and after the biocompatible layer is added, wherein the % open area between struts may be calculated by image analysis when using a digital microscope, for example. For example, an open area (in a two-dimensional image) may be an open area in an image taken along any side of the structure (e.g., top side, bottom side), or it may be an open area in an image taken through a cross-section of the structure (e.g., cross section through middle of the structure orthogonal to a top side and/or a bottom side). The open area may be characterized as the percent of the area (in the two dimensional image in question) that is open (i.e., the area in between and define by the structural struts).

A merely exemplary digital microscope and software associated therewith that can be used to determine or calculate % open area in two dimensions is the VHX 7000 Digital Microscope from Keyence, although other digital microscopes may be used to determine or calculate % open area, if they are adapted to determine of calculate the percent area that is open in a two dimensional image of the construct or through the construct, such as taken of a top or bottom surface thereof.

Figure 5:
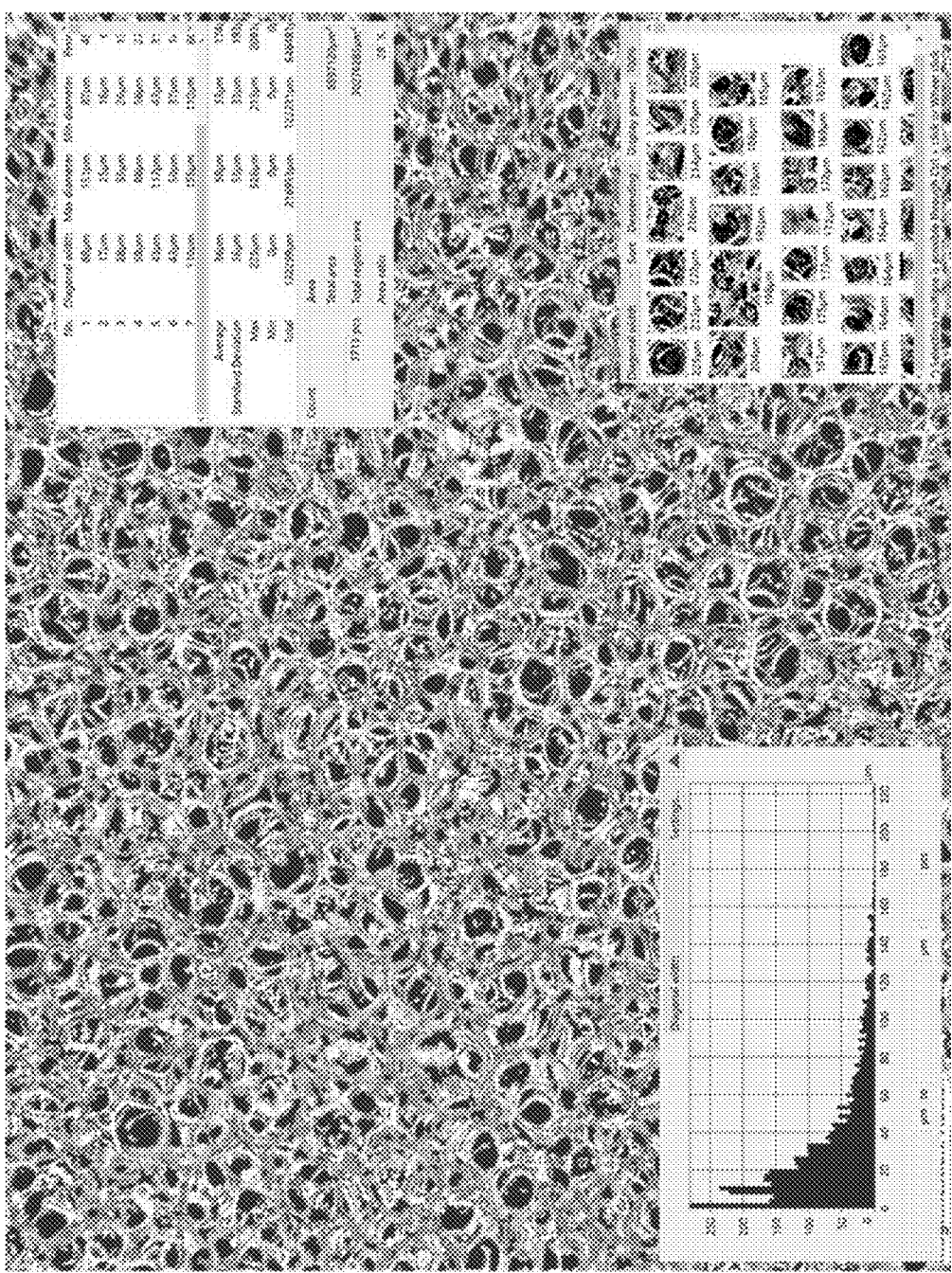
FIG. 5 illustrates an exemplary % open area calculation and image.

Some methods of determining % open area can include taking or obtaining a master porosity image, optionally with a high dynamic range function, which can help yield the best contrast between struts and pores (open area). A brightness extraction mode can be set to select the dark areas, which may correspond to the open pores. An auto area measurement image can be saved as a master measurement image. This can be used in subsequent measurements of samples and regions to produce repeatable measurement parameters. Some methods may include collecting images used a brightness extraction mode, with a threshold value of +10; elimination of small grains setting; and a 3× magnification. Calculating % open areas listed herein included selecting test areas for measurement using a rectangle geometry tool with a 5 mm×5 mm area for imaging. FIG. 5 illustrates an example of an image analysis area. The % open area for this particular construct using this particular image is listed as 28% as the "area ratio," which is an example of a % open area from 20-35%.

For example only, polyurethane may have 30% open area along a side of the template. Constructs have been constructed using methods herein, some of which have one or more sides (e.g., top and bottom) that are from 25-30% open area, which is an example of the biocompatible layer or coating not decreasing the porosity meaningfully. Any of the final constructs herein may have one or more sides that have an open area from 20-29%. Constructs have been constructed using methods herein in which cross sections are 25-30% open area.

Any of the constructs herein may also have a % open area in an image taken in a cross section orthogonal to a top side and a bottom side that is from 20%-30% open area.

Additionally, an additional way to help characterize the amount of biocompatible material that is added is a comparison of an open area of the construct relative to an open area of the template matrix material without the biocompatible layer. For example, some construct may have, in an image taken along a top or a bottom of the construct, an open area %, defined as open space between the plurality of struts, and wherein a matrix (e.g., polyurethane), in the absence of the conformal biocompatible coating, in an image taken along a top or a bottom of the polyurethane matrix, has an open area % defined as open space between the plurality of matrix struts. With any of the constructs herein, the difference between the construct open area % and the matrix open area % is less than 10%. In some embodiments the different is less than 5%. The relatively small difference in % open area highlights the relatively thin conformal biocompatible layers or coatings herein.

In any of the embodiments herein, the final construct may have a percent of open cells (porosity) greater than 90%, optionally more than 95% or more. This refers herein to the number of cells that do not have blocked pore windows and generally is referred to here as porosity.

An additional advantage of some of the constructs herein, which may be highly beneficial for some medical applications, is that the construct has a compliance or softness imparted to it that was not achieved with the matrix and biocompatible material by themselves. For example, increasing the compliance or softness of the construct can reduce friction between the construct and tissue against which it is placed, which can reduce or eliminate tissue abrasion. Additionally, increasing the compliance can make the construct easier to bend, which can help the construct better conform and make better contact with tissue or anatomy against which it is placed. Optional and exemplary method steps that can increase the compliance of the constructs herein are provided below.

For some uses, it may be beneficial or necessary that the final construct have wettability imparted to it when it comes into contact with water. For example, some medical uses may require that the construct have some degree of wettability, which may be imparted with a coating that is disposed about the biocompatible layer. Additionally, cross-linking of a coated may ensure that the coating is stable. Imparting wettability to the construct can improve the compatibility with tissue. Wettability can also improve fluid flow when the construct is in contact with tissue, which may be highly beneficial depending on the application.

In some optional examples, wettability is imparted by adding a hydrophilic hydrogel coating about the biocompatible layer. A hydrophilic hydrogel coating may have a thickness less than 5 microns, such as less than 3 microns. A hydrophilic hydrogel coating may be adapted to absorb water when exposed to water and thus impart wettability and the associated advantages thereof without meaningfully sacrificing the highly porous nature of the final construct.

Any of the final constructs herein may include a hydrophilic coating that is adapted to have a water content from 50%-95% when exposed to water, such as from 50% to 95%, 65% to 95, 70% to 95%, 75% to 95%, which can help provide a hydrophilic response).

Wettability of any of the constructs herein may optionally be characterized by the contact angle of water using the sessile drop technique when a surface of the construct is exposed to a drop of water. Contact angle refers to the angle measured between the surface and water applied to the surface, and generally the contact angle decreases with an increase in wettability of the surface. Constructs herein with an outer layer that is a conformal silicone coating (i.e., without an outer hydrogel layer) may have a contact angle from 90-110 degrees, such as from 90 to 95 degrees, due in part to hydrophobic nature of silicone. Constructs herein with an outer layer that is hydrophilic wettable layer may be from 5 to 35 degrees. For example, some hydrophilic coatings that have a water content from 50-80% in water may have contact angles from 20-35 degrees, and some hydrophilic coatings that have a water content from 81-95% in water may have contact angles from 5-20 degrees, for example.

An additional benefit of some of the constructs herein is that the final construct is very biocompatible (clean) with minimal amounts of, or no, leaching of chemicals, which may be highly beneficial or required in medical use applications when the constructs are in contact with tissue. Very clean, biocompatible constructs can ensure no toxicity when in contact with tissue. The very biocompatible nature of the constructs herein may be at least partially improved or imparted due to one or more manufacturing steps, examples of which are set forth below. For example, one or more silicone curing steps may be very efficient, as evidenced by extraction steps during which a very low level of unreacted (e.g., uncured) material is extracted (e.g., less than 5%). The one or more efficient curing steps can thus help minimize or eliminate leaching of chemicals when the construct is used in contact with tissue, which can make the construct safer to use.

In some aspects, the disclosure describes inventive porous structures (final constructs) having 40-99.6% porosity (i.e., % open cells), and preferably 60-99%, and most preferably 80-98% porosity. The structures can be open celled or semi-open celled with each cell on average containing more than 2 connections to neighboring cells and up to 18 connections to neighboring cells, with most preferably 5 to 12 connections to neighboring cells. The structures may have interconnection diameters for the most part ranging between 5-2500 um, more preferably 15-1500 um, and most preferably 25-900 um, and averaging 50-900 um, and more preferably 150-800 um, and most preferably 250-650 um. The structures should also contain pore sizes ranging from 50-3500 um, more preferably 150-2500 um, and most preferably 250-1500 um. The structure may optionally in some alternatives be dissolvable in its entirety or into a liquid, gel, or suspension form by a solvent, more preferably an organic solvent such as DMSO (dimethylsulfoxide), NMP (N-methylpyrrolidone), DMF (N,N-dimethylformamide), Dioxane, Acetone, Acetonitrile, Hexane, Toluene, Chloroform, Dichloromethane, Isopropanol, or Ethanol, with most preferably Acetone, Acetonitrile, DMSO, NMP, or DMF, or as a mixture of any of the aforementioned solvents. Any of these structures will be referred to herein as a matrix material, or a derivatives thereof.

The disclosure herein also describes innovative processes that include surrounding individual structures of the matrix material with a coating material, which may be biocompatible (e.g., silicone) by coating or impregnation. The coating process may be conducted using the coating material in a liquid state, or liquefied construct material, a solution state, a gel state, an emulsion state, a suspension state, or a mixture state to fully or partially impregnate the pores of the matrix material, followed by removal of excess such that a conformal coating (optionally biocompatible such) remains on the struts of the template matrix and allows for non-occlusion of the pores.

The coating material be comprised of one or more of a meltable polymer, a dissolvable polymer, a meltable or dissolvable polymer mixture, a meltable or dissolvable polymer solution, a meltable or dissolvable monomer mixture or solution, a meltable or dissolvable prepolymer mixture or solution, a meltable or dissolvable oligomer mixture or solution, or a combination of any of the aforementioned with a polymer, ceramic, or metal in powder, gel, or liquid form. In some specific embodiments the polymer is a solution of a dissolvable polymer in an organic solvent and the dissolvable polymer is deposited unto the matrix material as the excess construct material is removed and the solvent evaporates. In another specific embodiment a molten material is impregnated into the structure of the matrix material and wets the internal structures of the matrix material due to surface tension. In yet another embodiment the coating material is in an emulsion and leaves the emulsion in the presence of the matrix material depositing thereafter on the internal structures of the matrix material. In some general embodiments, a polymer comprising a part or a whole of the construct material can be chitosan, chitin-chitosan copolymer, a PLGA copolymer, a polycaprolactone homo polymer or a copolymer of polycaprolactone and another polyester, a silicone pre-polymer, a silicone polymer, polyethylene, Viton pre-polymer, PVDF, polystyrene, polyvinyl alcohol, polyvinyl alcohol-acetate copolymer, an olefin polymer or copolymer, a polysaccharide or a copolymer containing a polysaccharide, a polyester or polyester copolymer, a polyether or polyether copolymer, a polyethyleneamine, an alginate, a polycarbonate, polyamide, polyamine, polyurea, or a copolymer, blend, a linear or crosslinked hydrogel homopolymer or copolymer, a linear or crosslinked hydrogel homopolymer or copolymer containing a siloxane component, a linear or crosslinked hydrogel homopolymer or copolymer containing an additive such as silver nanoparticles or silver microparticles, polyelectrolytic complex of any one or more of the aforementioned polymers. The coating material can optionally contain up to 80% by volume of a ceramic or metal in powder of microfiber form. In some embodiments, the ceramic powder is 5 nm to 100 um in average diameter, more preferably 25 nm to 25 um of average diameter, and most preferably 150 nm to 10 um in average diameter. In some embodiments, the ceramic powder is in the shape of a fiber, or a spherical shape, or a dendritic shape. In some embodiments, the ceramic powder is a sodium chloride salt, calcium carbonate, silica, alumina, zirconia, diamond dust, aluminum nitride, aluminum carbide, or a mixture of any one or more of the aforementioned. In yet other embodiments, the metal powder ranges in the sizes of the aforementioned ceramic powder and has the shapes of the aforementioned ceramic powder. In other embodiments the metal powder is a gold powder, silver, copper, aluminum, or iron. In other embodiments the metal powder is an alloy such as tin, steel, nitinol, nicoloy, algiloy, or other alloy. In yet other embodiments the material contains bioactive agents such as small molecules pharmaceuticals, peptides, small molecule chemical agents, large molecules such as antibodies, traps, proteins, DNA, RNA, or the like.

Any of the exemplary methods of manufacture herein may also include a process for obtaining a desirable microstructure of the final construct, wherein the coated or impregnated construct material is removed in a manner to retain only a desired amount of the construct material to attain a desired structure of the final construct material. Specifically, in some embodiments herein, the coating material fills the pores and matrix material fully and is then partially removed such that it is at a level of 60-80% of the original by volume, in other embodiments, the coating material is removed to a level of 40-60% of the original by volume, in yet other embodiments the coating material is removed to a level of 20-40%, in yet other embodiments the coating is removed to a level of 10-20%, and yet in other embodiments the coating material is removed to a level of 3-10% by volume.

After the removal of the material, one or more of a solidification, curing, or polymerization step may then be performed to the coating material. In one embodiment, the coated or impregnated construct material, that is in the form of a solution, mixture, gel, emulsion or suspension, is solidified by freeze drying. In another embodiment, the coating material is solidified by drying, precipitation, separation from the solution, emulsion, suspension, mixture, or suspension phase. In yet another embodiment, the material is polymerized before or after the solidification process. In yet another embodiment, the material is crosslinked before or after the solidification process. The solidified coating material can conformally coat the internal structure of the matrix material, or form a different structure from the matrix material. In a preferred embodiment, the coating material predominantly coats the matrix material in a conformal manner. In some embodiments, solidification is assisted by vacuum, in yet other embodiments, a precipitation is facilitated by application of a liquid, gas or temperature change. In yet another embodiment, the solidification is facilitated by a polymerization reaction, which is optionally facilitated by heat and/or UV radiation, with or without introduction of a separate crosslinking agent. In yet another embodiment, solidification is facilitated by crosslinking after exposure to plasma. In some specific embodiments a heat of about 80% of the carrier solvent is applied; in other specific embodiments molten construct polymer is cooled below the freezing point; in yet other embodiments a prepolymer is heated to initiate a crosslinking or polymerization reaction.

In some embodiments a coating or impregnation step is repeated after the solidification, precipitation, curing or gelation step to increase the amount of coating material within the microstructure of the matrix material, such as by approximately 20-50%, or approximately 50-100%, or approximately 100-200%, or approximately 200-500% of the original construct material by weight. In some embodiments, the first and optional subsequent coating or impregnation steps, which there may be optionally 2-10 of, and in some cases 10-50 of, are not the same, and may include using different coatings or impregnation materials, or a different subsequent drying or solidification step. Specifically, in one optional embodiment, a first impregnation step is made using a 4% solution of chitosan in acetic acid, dried to remove at least 90% by weight of the acetic acid, and a second impregnation step is made with 2% solution of alginate, that is once again dried to at least 95% solids by weight after the impregnation. In other specific embodiments the first or any of the subsequent drying, solidification, or polymerization steps are followed by a chemical modification, or neutralization, or a chemical reaction, or a physical state change.

After one or more coating or impregnation, and drying, solidification, and/or polymerization steps, the matrix material, in some embodiments, optionally may be at least partially removed by a solvent that can dissolve the matrix material. The optional removal may take place at ambient conditions or at elevated temperatures such as approximately 40-60° C. or 60-80° C. or 80-120° C. and optionally with agitation. The targeted removal of the matrix material may be anywhere from 0.5-100%, preferably 20-100%, and most preferably from 80-100% by weight.

Figure 2:
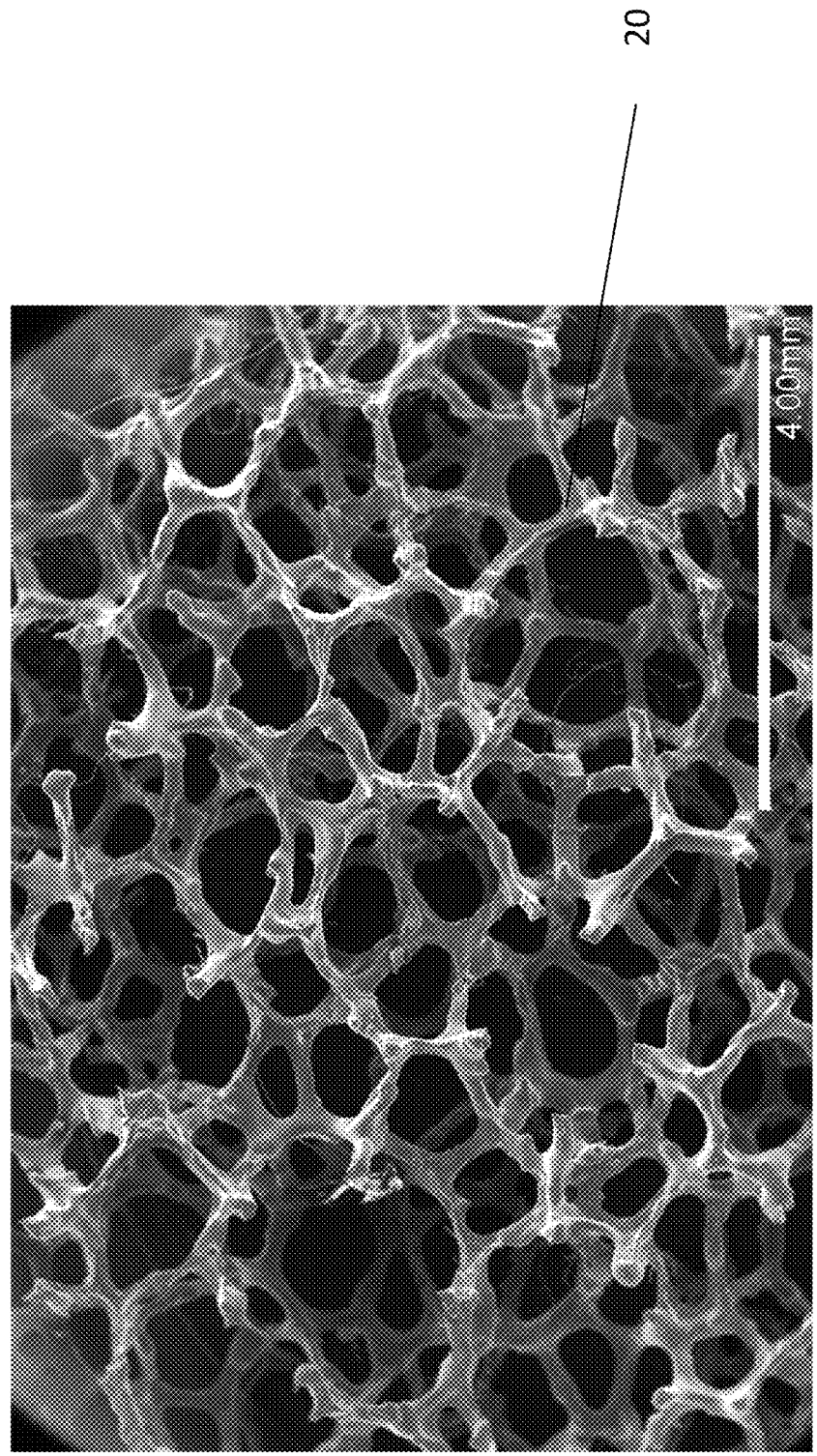
FIG. 2 illustrates a scanning electron micrograph image of an exemplary open cell silicone-coated construct.

FIG. 1 shows a high magnification view 1 of the structure of an exemplary commercial polyurethane foam. Only one exemplary strut 10 is labeled, and the pores are the open space between the struts. FIG. 2 shows a high magnification view 2 of an exemplary structure of a construct including a silicone coating, with only one of the exemplary struts 20 labeled. The pore are the open spaces between and defined by the struts. It can easily be seen that the construct of FIG. 2 has a similar appearance to the open cell interconnected structure present in the polyurethane foam in FIG. 1. FIG. 2 represents any of the constructs including a matrix and conformal coating layer described herein.

In the embodiments in which the matrix material is at least partially and optionally removed, after the optional removal of the matrix material, an additional coating or impregnation step may be performed to accomplish one or more of: 1) filling the voids left by the original matrix material or; 2) add external reinforcement to the struts of the construct material. During additional optional coating steps, 5-100% of the original voids left by the matrix material may be filled, and in some preferred embodiments 15-100%, and optionally most preferably 50-95%. Additional coating steps can be followed by one or more of an additional solidification, curing, polymerization, and/or crosslinking step, and may be followed by additional coating or chemical modification steps thereafter.

At any time after any of the drying, polymerization, crosslinking, gelation, solidification, and/or curing steps herein, additional post processing steps may be performed. In some embodiments, post-processing steps may be one or more of neutralization, a chemical modification, or washing, sterilization, purification, drying, or solvent removal steps, including any combination thereof.

One aspect of the disclosure includes the final (or finished) construct resulting from the exemplary processes herein. For example, a final construct may include a porous structure, optionally having 50-99% porosity, more preferably 60-98.5% porosity, and most preferably 80-98% porosity.

The final constructs herein may also contain interconnected or semi-interconnected pores with each cell on average containing more than 2 connections to neighboring cells and up to 16 connections to neighboring cells, with most preferably 5 to 12 connections to neighboring cells. The finished constructs herein may include interconnection diameters for the most part ranging between of 5-2200 um, more preferably 15-1500 um, and most preferably 25-800 um, and averaging 50-800 um, and more preferably 150-750 um, and most preferably 250-600 um. The finished constructs herein may also contain pore sizes ranging from 50-3000 um, more preferably 150-2000 um, and most preferably 250-1200 um.

In some embodiments, struts supporting the construct in its final state are in the range of 10-50 um in their thinnest section, in yet other embodiments the struts are 25-150 um in their thinnest section, in yet other embodiments the struts are 50-250 um in their thinnest section, and in yet other embodiments the struts are 150-500 um in their thinnest section. On average, the struts in their thinnest section can average between 25 and 1000 um, more preferably 35 to 800 um, and most preferably 50-600 um.

In some embodiments, the final construct contains voids within the final struts of 10-150 um on average in their thinnest section, in yet other embodiments the voids are 5-75 um, and in yet another embodiment the voids are 0.5-50 um. In general the voids are 0-100% of the original size of the matrix material strut, and more preferably 0-80%, and most preferably 0-45% of the original size of the matrix material strut.

The disclosure that follows includes exemplary steps that may be performed during the manufacture of constructs described herein during which the template material is not dissolved away. While the steps may be described in an order, it is understood that there may be some variability in the order. Constructs manufactured using one or more of these method steps may provide one or more of the benefits described herein when used medically and in contact with tissue, such as improved biocompatibility, highly porous, optional enhanced smoothness, and optional enhanced wettability.

Some methods of manufacture include starting with or providing a porous template matrix, which is some cases may be a highly porous polyurethane matrix. The methods may include forming a porous template material do the desired dimensions. Forming the template material may include cutting the template to the desired dimensions to form a sheet of template material that may have a height relatively much less than a length and width dimension.

Some methods may include preparing a biocompatible material that will be used to create a conformal biocompatible layer or coating on the porous template material. In some examples the methods may include preparing a silicone dispersion, optionally with xylene as a solvent. In some methods the dispersion has a relatively low percentage of silicone, which may facilitate the creation of a relatively thin silicone layers, advantages of which are provided herein (e.g., not sacrificing the highly porous nature of the final construct). In some examples, the dispersion may be from 5 to 35% silicone, with a xylene solvent. In some example, the dispersion may be from 10 to 35% silicone, such as 15% to 25% silicone. In some particular examples, the dispersion includes 20% silicone resin to 80% xylene solvent, but other relative percentages may be used. Optionally the dispersion may be degassed to remove bubbles.

In some examples, a silicone dispersion may be coated onto the porous template material. This may optionally include submerging an open or semi-open celled porous template into a silicone dispersion to expose the template structure to the silicone dispersion, wherein the template structure comprises a plurality of template struts that define a plurality of template pores. The method may include, after submersion, allowing the silicone to pass into the plurality of template pores. Subsequent in time, excess dispersion may be removed, optionally with a spinning process that removes excess dispersion. The method may further comprise curing the biocompatible material to form at least part of a conformal layer on the struts of the template matrix. The conformal layer extends completely around the struts of the matrix. The curing step forms a plurality of construct struts that include the conformal biocompatible coating (e.g., silicone) on the plurality of template struts, wherein the plurality of construct struts define a plurality of construct pores.

One or more coating and curing steps may additionally be performed to add to the conformal biocompatible layer. For example, the method may include one additional coating and curing step, two additional coating and curing steps, three additional coating and curing steps, or more, such as from four to ten additional coating and curing steps.

After the one or more curing steps (depending on how many coating steps were performed), an extraction step may be performed to remove any uncured biocompatible material such as silicone (wherein the extraction may also remove some minor amount of the template material). For example, the methods may include an extraction in xylene.

An unexpected result from construct development related to this disclosure was that the compliance or softness of the construct can be enhanced during the manufacturing thereof, and particularly when exposing sample constructs to dimethylsulfoxide ("DMSO"). Additionally, this step also enhanced smoothness to the surface of the construct. DMSO was initially used in the manufacture of some constructs for which the matrix was dissolved (examples of which are included herein; e.g., dissolved polyurethane matrix). An unexpected enhancement in softness or compliance as well as its smoothness of the matrix-coated construct was observed when the construct was exposed to DMSO. Depending on the intended use of the final construct, it may be beneficial to soften the construct (making it more compliant), exemplary benefits of which are described above. For example, making it more compliant may allow it to better adhere or conform to tissue against which it is being applied. Additionally, increasing construct smoothness can lead to lower friction compared to the pre-coated template and in addition to most commercially-available foam materials or structures. When used in medical applications, lower friction can lead to less abrasion when in contact with tissue. With some template/biocompatible material constructs, and depending on the use, the compliance and/or smoothness after adding the biocompatible layer may not be the desired compliance and/or smoothness. In some examples, the construct may be exposed to a compliance and/or smoothness enhancing agent, which may make the construct softer and more compliant as well as smoother. Exemplary compliance and/or softness enhancing agents include DMSO, dimethylformamide, gamma-butyllactone, and dimethylacetamide. In some examples the construct may be exposed to DMSO and acetone solution. For example, the construct may be treated for 30 minutes, an hour, and hour and a half, or more. The compliance and/or softness enhancing agent may be extracted with water following the treatment. An exemplary benefit of exposure to DMSO is that for some constructs the exposure may increase both compliance (softness) as well as smoothness while only requiring exposure to one material (e.g., DMSO), which can simplify manufacturing.

In some applications, it may be desirable for the construct to have wettability imparted to it, which may help when in contact with water or bodily fluids (additional benefits of which are described above). For example, some constructs may include a hydrogel coating added to it to impart wettability to the construct. In some examples, a hydrogel coating may be applied to the surface of a conformal silicone layer. The hydrogel coating may be covalently bonded to the silicone, and is also covalently bonded and crosslinked to itself. This can impart wettability to the surface of the final construct when in contact with water or bodily fluids. The wettability imparted may enhance the effect of the construct depending on the medical application. For example, the wettability make help the construct adhere better (stronger adhesion forces) to the tissue against which it is placed.

In some examples, the hydrogel layer is a hydrophilic layer that is covalently bonded to the silicone and is also covalently bonded and crosslinked to itself.

The hydrogel layer may comprise one or more hydrophilic monomers, for example, including but not limited to PEGA, HEA, HEMA or NVP. For example only, a hydrogel monomer mix may first be prepared that includes 50% hydrogel monomer mix and 50% xylene. In some non-limiting examples, the monomer mix may include 50% polyethyleneglycol acrylate (e.g., PEGA 480), 50% 2-hydroxyethyl acrylate (HEA), a cross-linker (e.g., allyl methacrylate (AMA)) and an initiator (e.g., AIBN initiator). In some embodiments the cross-linker is present in the mixture at about 0.5%, and the initiator is present at about 1%.

Before forming the hydrophilic layer, the biocompatible layer (e.g., silicone) may be treated to prime the layer for reacting with the hydrophilic material. For example, a conformal silicone layer may be corona treated one or more times, which changes the surface chemistry of the silicone and allows it to covalently bond to one or more hydrophilic monomers.

After surface treating the construct, the construct may be immersed in a coupling agent, such as a 5% silane in ethanol coupling agent. The exposure to the coupling agent allows for reactivity between the silicone and the monomer mix and thus the formation of covalent bonds therebetween. In some examples the silane coupling agent may comprise 3-(trimethoxysilyl) methacrylate.

The construct may subsequently be cured, such as in an oven at temperature.

The construct may then be treated with the hydrogel monomer mix, dried, and cured. Following curing an extraction step may be performed to remove uncured monomers, such as with ethanol extraction. The construct now includes a hydrophilic layer surrounding the silicone layer.

The examples provided herein may be used to manufacture different types of constructs, the particular methods of which may be based on the intended use of the application. For example, constructs for medical uses may optionally include method steps that impart characteristics that are advantageous for certain medical applications. Some constructs may have non-medical uses, and thus there may not be a need or desire to impart one or more characteristics to those constructs. Additionally, while the disclosure thus far may have focused on constructs for which a matrix material is not dissolved away, some examples that follow include a step that removes at least part of the matrix, which provides for alternative and optional constructs herein.

Example 1

The exemplary sequence provided includes steps of this example 1. Add 18.0 grams Wacker 625 Part A silicone and 2.0 Wacker 625 Part B silicone to 80.0 g xylene in a PET container. Stir via magnetic stirrer until complete dispersion occurs. Pour dispersion into low profile soaking container. Place into vacuum oven and pull a vacuum (−75 cm Hg). Allow to remain at full vacuum for 5 minutes. Vent the unit to ambient pressure. Repeat vacuum—vent cycles 2 more times.

In this example the matrix is a polyurethane matrix. Polyurethane stock foam sheets are stored in a black plastic bag until ready for use. Exposure to ambient sunlight and air should be minimal during storage. Remove single polyurethane foam sheets and inspect visually for warpage, and preferably only use flat sheets. Place polyurethane foam sheet onto paper cutter and cut into 6×6 inch pieces (other sizes may also be cut depending on the application). Assemble the foam sheets into a pile and place an opaque material (paper, fabric, etc.) on top until ready for use. This minimizes exposure to sunlight and particles.

Place a foam sheet into the dispersion created above and allow to fully saturate. Remove foam sheet from dispersion by handling one corner (e.g., with tongs). Allow excess to drain until dropwise formation. Place foam sheet into spin dryer so that the bottom edge is parallel to the table. Repeat with remaining sheets until spin dryer reaches capacity. Activate and allow to spin for 1 second. Reorient samples vertically (bottom to edge allowing same side to remain constant). Activate and allow to spin for 1 second. Remove all foam samples and place on curing rack. Preheat the oven to 50 degrees C. Place the rack containing the samples into the oven. Dry at 50 degrees C. for one hour. Ramp temperature to 110 degrees C. and allow to remain for two hours. Remove rack from oven and allow samples to cool to room temperature before proceeding Repeat the dispersion-coating-curing cycles until three total silicone coats are applied. Prepare five xylene baths, approximately 500 ml per 3 foam samples. Soak each silicone composite sample in the first bath for one hour. Remove sample and blot dry with microfiber towel or equivalent (low lint). Place sample in next bath and repeat. Total process is 5 baths×3 samples yields extracted samples after approximately 5 hours. Place in oven at 80 degrees C. for approximately 4 hours. Add acetone to container, volume depends on size of the container. Add composite sheet and allow to fully saturate. Add additional acetone, if needed, until height is about ¼ inch in container. DMSO is added to reach an approximate ratio of 1/1 DMSO/acetone by volume. DMSO is added down the inside wall of the container to ensure minimal bubble formation and minimal solvent shock to the sample(s). Place in vacuum oven and pull to full vacuum. Boiling will be seen. Vent to ambient pressure. Remove container from vacuum oven and place in a water bath at room temperature. Heat the water bath to 80 degrees c. and allow acetone to boil off (bubbles will be seen). Time for complete acetone removal is approximately 15 minutes. Allow to remain at this temperature for one hour. Remove samples from hot DMSO and carry onto next step. Preheat DI water to 50 degrees C. Add each foam unit to the DI water and submerge. Allow unit to be soaked in water for 15 minutes with slight agitation. Remove foam unit from water and blot dry with cloth. Place unit in ethanol wash 1 and submerge for 15 minutes. Remove unit from ethanol wash 1 and blot dry before transferring into a fresh container of ethanol 2. After submersion for 15 minutes in ethanol wash 2, remove unit and blot dry before transferring into 3rd container of ethanol. After exposure to ethanol wash 3 for 15 minutes, remove unit and bot dry. Blot each unit with a cloth and lay flat on a rack and place in oven at 50 degrees C. After one hour, remove units from oven and carry onto the next step.

The following abbreviations are used in this example: PEGA 480=poly(ethyleneglycol) methyl ether acrylate, MW=480; HEA=2-hydroxyethyl acrylate; AMA=allyl methacrylate; AIBN=2,2'-Azobis(2-methyl-propionitrile); TPM=3-(trimethoxysilyl)propyl methacrylate. The example includes the following exemplary composition for an optional hydrophilic layer. (Monomer Mix): PEGA 480, HEA, AMA 50/50/0.5%. AIBN 1%. Grams of AMA is based on total grams of PEGA 480 and HEA, grams AIBN is based on total grams of PEGA 480 and HEA.

95% ethanol/water is acidified with glacial acetic acid until pH 4.0 is achieved. Solution of 5% (g) of silane coupling agent in 95% ethanol is prepared. Stirred is allowed for 5 minutes to form silanol. Silicone composite is corona treated 3 passes per side, approximately 1 sec per pass. The silicone-polyurethane composite from is immersed in the silanol solution for 3 minutes until full saturation occurs. Sample is removed and placed in oven at 80 degrees C. for one hour followed by 30 minutes at 110 degrees C. A 50/50 (g/g) mixture is prepared of the hydrogel monomer mix in xylene. The solution is stored until the appropriate step. Dry foam construct sample are placed in the monomer mix solution until full saturation. The sample is removed and blotted using a microfiber towel. Sample is placed in oven at 80 degrees C. for two hours followed by 110 degrees for 4 hours.

Treat each coated sample with 95% ethanol by immersion into a bath. Total treatment time is 15 minutes per bath, 3 baths total. Samples are blotted dry between baths using a paper towel. Sample is dried in oven at 80 degrees C. for one hour.

Table 1 below illustrates sample constructs produced using techniques described herein, including properties of the construct. Table 1 includes final construct properties, as well as the biocompatible layer (in this case silicone) thickness in microns. Table 1 also includes the optional hydrogel thickness in microns and water content. The samples in Table 1 were manufactured with polyurethane foam templates that were 100 PPI and ⅛ inch thick.

Figure 6:
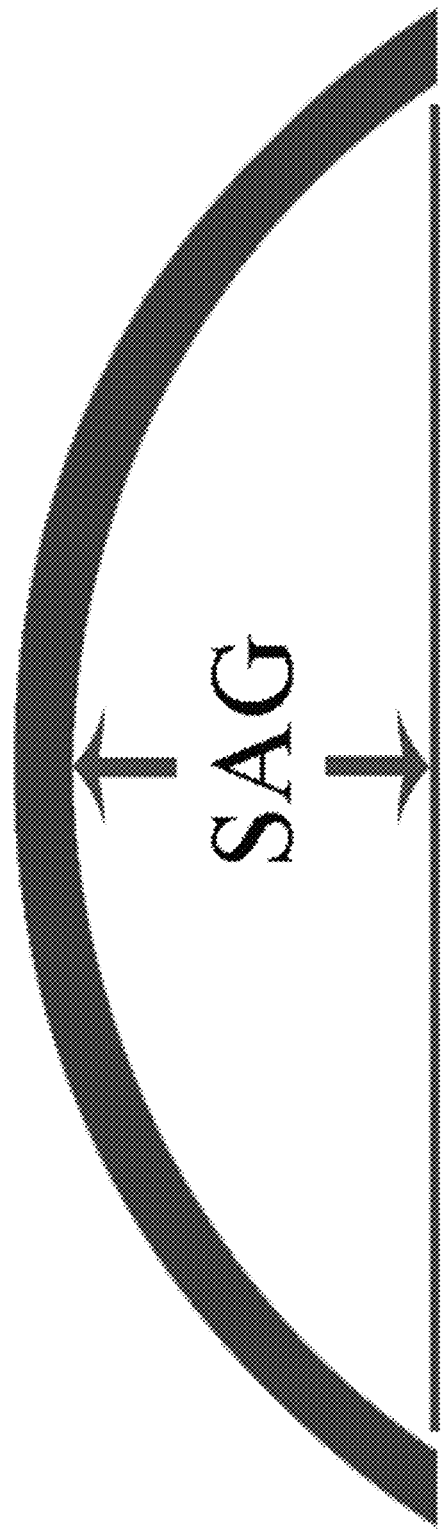
FIG. 6 illustrates a measured SAG of constructs herein.
Figure 7:
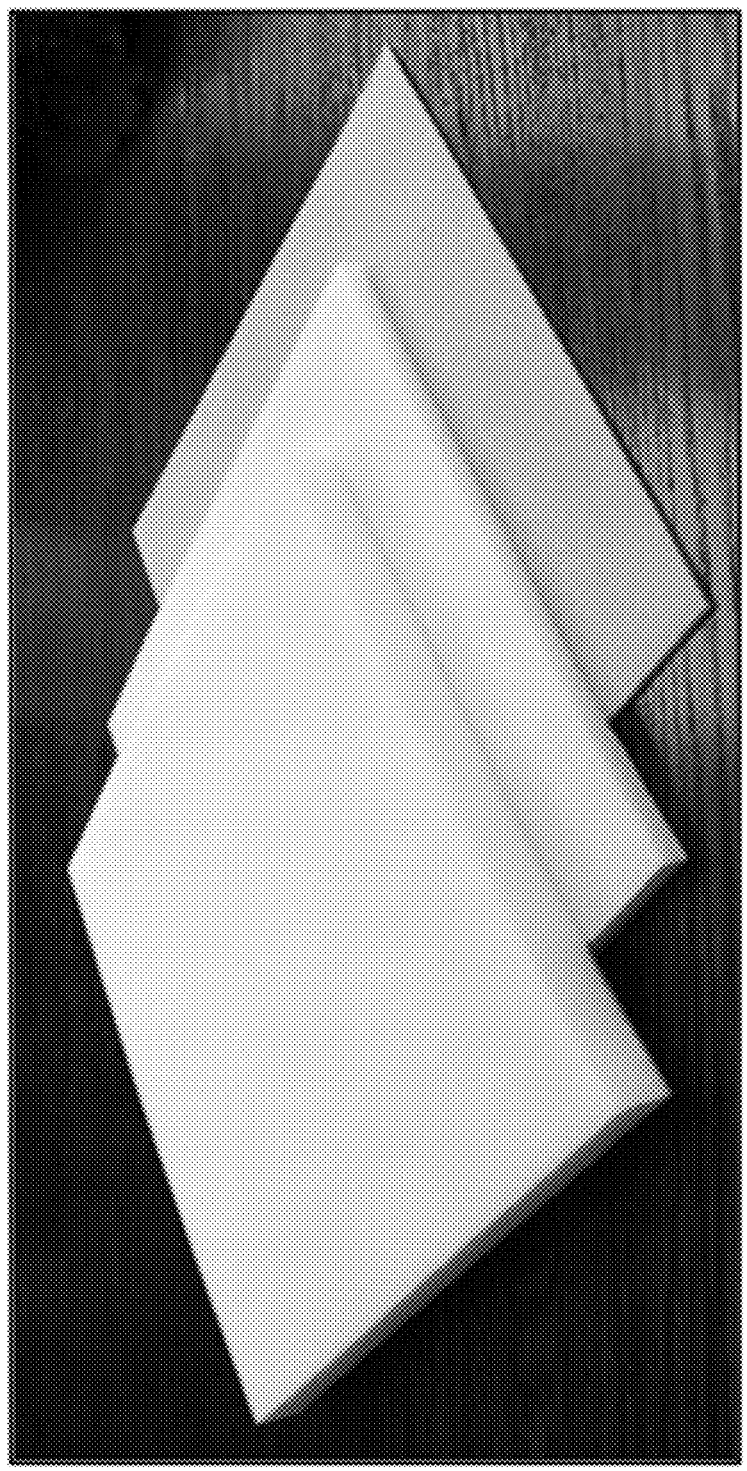
FIG. 7 illustrate exemplary constructs that include a matrix and a conformal biocompatible coating, as well as a hydrophilic coating thereon.

As shown in Table 1, the porosity for all of samples 1-12 is 95% or greater, exemplary benefits of which are described herein. In fact, for ten of the twelve samples the porosity is 98% or 99%. The densities of these twelve samples are all from 0.01 g/cc to 0.2 g/cc, such as from 0.01 g/cc to 0.15 g/cc, or such as from 0.05 g/cc to 0.18 g/cc, such as from 0.05 g/cc to 0.15 g/cc. As shown in Table 1, these exemplary samples have strut thicknesses from 66 microns to 80 microns, which are examples of strut thickness from 35 microns to 90 microns. Table 1 also shows open area % of the twelve samples being from 22% to 29%, which are examples of open area % from 20% to 35%, and which is described in more detail herein. Table 1 also includes tested and measured "SAG" for the twelve samples. SAG as used in this context refers generally to property indicative of the amount of droop of the sample. For these samples, SAG was measured using a 6×6×⅛ inch construct sample. An 8-inch rod with ⅛ inch diameter was placed down the middle of the sample sheet. The sheet is balanced by the rod, as shown in illustrative FIG. 6, which elicits some amount of drooping. "SAG" is the measurement between the center, where the rod is located, and the lowest point of the material during drooping. For the samples in Table 1, the SAG measurements were from 50 mm to 56 mm, which are examples of constructs with SAG from 45 mm to 60 mm. Table 1 also lists illustrative thicknesses for the biocompatible layer, which in these samples is silicone. In these examples, the thicknesses are from 3 microns to 12 microns, which are examples of conformal biocompatible layer thicknesses from 1 micron to 20 microns, such as from 1 micron to 15 microns.

Table 1 also lists optional and exemplary hydrogel (e.g., dry hydrophilic layers that are wettable when exposed to water) thicknesses and water content when exposed to water. As shown, the samples had thicknesses from 2 microns to 4 microns, which imparts wettability without significantly reducing porosity. The thickness shown are examples of thickness from 1 micron to 5 microns, although in some embodiments the hydrogel thickness may be up to 10 microns.

Table 1 also list exemplary hydrogel layers that may have 50% to 95% water content when exposed to water. In general, the hydrophilic hydrogel layers are dry, but impart wettability when absorb water when exposed to water.

Table 1 also lists exemplary materials for the construct, with three samples prepared with each of the listed materials.

TABLE 1

| # | Construct | | | | | Silicone Coating Thickness (microns) | Hydrogel | |
|---|---|---|---|---|---|---|---|---|
| | Density (g/cc) | Strut Thickness (microns) | Open Area (%) | SAG (mm) | Porosity (% Open Cells) | | Coating Thickness (microns) | Water Content (%) |
| Wacker Elastosil 625 Silicone, N-Vinylpyrrolidone, 2-Hydroxyethyl methacrylate | | | | | | | | |
| 1 | 0.11 | 72 | 28 | 52 | 99 | 5 | 2 | 50 |
| 2 | 0.12 | 74 | 27 | 52 | 99 | 8 | 2 | 62 |
| 3 | 0.13 | 80 | 22 | 56 | 98 | 12 | 3 | 78 |
| Nusil Med-4820, N,N-dimethylacrylamide, 2-Hydroxyethyl methacrylate | | | | | | | | |
| 4 | 0.10 | 75 | 28 | 50 | 99 | 4 | 2 | 72 |
| 5 | 0.11 | 72 | 29 | 51 | 99 | 6 | 3 | 78 |
| 6 | 0.11 | 70 | 28 | 51 | 99 | 5 | 3 | 82 |
| Wacker Elastosil 625, poly(ethyleneglycol) methyl ether acrylate, MW = 480, 2-hydroxyethyl acrylate | | | | | | | | |
| 7 | 0.12 | 72 | 26 | 51 | 98 | 8 | 2 | 80 |
| 8 | 0.10 | 68 | 28 | 51 | 99 | 4 | 4 | 79 |
| 9 | 0.11 | 70 | 28 | 50 | 99 | 5 | 3 | 78 |
| Wacker Elastosil 625, N-Vinylpyrrolidone, poly(ethyleneglycol) methyl ether acrylate, MW = 480, 2-hydroxyethyl acrylate | | | | | | | | |
| 10 | 0.12 | 71 | 26 | 52 | 96 | 5 | 3 | 80 |
| 11 | 0.12 | 68 | 27 | 55 | 99 | 3 | 2 | 85 |
| 12 | 0.12 | 66 | 26 | 51 | 97 | 4 | 2 | 84 |

It is of note that there are different types of polyurethane foams available, including variations in pores per inch ("PPI"). For example, some polyurethane foams have 100 PPI, while some polyurethane foams have 40 PPI, for example. As the PPI increases, the pore diameter decreases, generally, and vice versa. The constructs herein and concepts related thereto may be applied to polyurethane foams having a variety of PPI, examples of which are listed in Table 2. Any of the disclosure or claims herein (or claims that may be written based on the disclosure) may include or incorporate or take into account the dimensions in Table 2. For example, constructs described in Table 1 may be based on 100 PPI polyurethane matrices. Alternative matrices that are, for example, 40 PPI may have larger pore diameters, and may also have larger interconnections pore diameters, for example, as illustrated in Table 2. Strut thickness of relatively lower PPI matrices will generally be larger, as shown in Table 2. Any of the claimed ranges may thus be modified according to take into consideration a lower PPI matrix, such as a 40 PPI matrix.

TABLE 2

(in microns) - Exemplary polyurethane foams

| Sample | Strut Thickness (microns) | Interconnection Pore Diameter (Microns) | | Pore Diameter (microns) |
|---|---|---|---|---|
| | | Small | Large | |
| 100 PPI polyurethane | 41-62 | 112-125 | 146-203 | 237-512 |
| 40 PPI polyurethane | 70-88 | 185-225 | 285-290 | 703-880 |

Table 2 illustrates the variation in strut thickness, interconnection pore diameter, and pore diameter based on the matrix PPI. Table 2 thus provides support for a variance in the final construct dimensions, which may depend on the particular polyurethane matrix that is part of the final construct.

Example 2: Process for Making an Exemplary Final Composite Construct

An open celled polyurethane foam sheet (an example of a matrix material) having the following parameters is obtained commercially: ⅛ inch thick, 12×12 inch length× width, 100 PPI (pores per inch). The polyurethane foam sheet is allowed to soak in a dispersion of Nusil MED 4830 in xylene, 15% solids based on total mass of dispersion (an exemplary silicone material). After complete impregnation of the dispersion into the pores, the resulting foam is transferred to a grate and excess dispersion removed via an air knife. The resulting foam is cured by being placed on a rack in an oven and subjected to 150 degrees C. for 4 hours. The dry and cured construct is subjected to two additional cycles of silicone soaking, excess removal, and curing. The resulting construct is placed in a container of DMSO at 60 degrees C. for one hour. Subsequently the material is rinsed in DI water, 2×, matted down with lint-free material to remove excess water, and finally rinsed 3× with 95% ethanol. The material is placed on a rack in an oven at 50 degrees C. for one hour. The final construct yields a soft & pliable open celled foam having a composite structure of silicone on a polyurethane matrix. This is an example of a construct that does not have a hydrophilic layer added.

Example 3: Process for Making an Exemplary Optionally Coated Composite Construct Each side of the foam material generated in EXAMPLE 2 is corona treated for 60 seconds at a 0.5 inch electrode distance to the surface of the foam. The open celled foam is then soaked in a solution of ethanolic monomer mix 80% ethanol: 20% monomer mix. Composition of the monomer mix is: 80% N-vinyl pyrrolidone (NVP): 20% 2-hydroxyethyl methacrylate (HEMA) containing 0.5% allylmethacrylate and 0.5% AIBN initiator. Crosslinker and initiator concentrations are calculated based on total mass of NVP and HEMA. Excess ethanolic monomer mix is removed via an air knife. The foam was subsequently placed in an oven on a rack at 60 degrees C. for 4 hours. The optional crosslinked hydrophilic polymer coating imparts wettability to the silicone surface of the porous construct, exemplary advantages of which are set forth herein.

Example 4: Process for Making Final Construct

In the third example, a polyurethane foam template (e.g. matrix material) with a degree of crosslinking sufficient to maintain mechanical integrity, but not inhibit dissolution by dimethyl sulfoxide at room temperature, and 97.8% porosity, an average pore diameter of 800 um, an average number of interconnections per pore of 9, and an average interconnection diameter of 400 um, is coated with a 91% deacetylated chitosan solution containing 2% wt/wt chitosan in 1% wt/wt acetic acid and 99% wt/wt deionized water by decanting the solution over a 30 cm by 30 cm sheet of polyurethane foam with a thickness of 10 mm. The foam is squeezed by a set of rollers to a thickness of 15% during the decanting to allow maximum impregnation of the chitosan solution, and then again to 25% of original thickness to remove the excess chitosan solution, repeatedly until the pickup by weight is 10% of the original polyurethane foam. The impregnated foam is then dried at 37 C for 12 hours and neutralized by a wash with excess 20 molar ammonia in ethanol solution. The impregnation, drying, and neutralization processes are repeated 8 times to attain a pickup of 80% of the original polyurethane foam by weight. The impregnated foam is then submerged in DMSO at 40 C for 6 hours, and subsequently washed with DI water at 100 C for 3 hours with agitation. The dissolution and washing process is repeated 3 times.

Example 5: Process for Making Exemplary Final Construct with Void Filing

This example provides a method of forming a construct that includes a process of removing at least part of the matrix. In the fifth example, a lightly crosslinked polyurethane foam, dissolvable by DMF at 37 C in 4 hours, and containing 98% porosity, an average pore size of 1300 um, an average interconnection diameter of 800 um, and an average number of interconnections per pore of 7.4, is coated with a functionalized Viton prepolymer of 30 cP in Acetone by metered decanting. The polyurethane foam is compressed by a filter grate containing pores of 1000 um to 30% of its original displacement and released as the coating is applied to cause maximum impregnation. After release to 100% of original height, the filter grate applies a compression of 50% of height and a house vacuum is applied from the bottom of the polyurethane foam to remove the excess Viton prepolymer solution. After the impregnation process is completed the material is polymerized at 120 C for 4 hours, and dried at 80 C for 6 hours. The base foam is then dissolved in DMF with agitation, and the resulting construct containing central voids is washed in acetone and water in repeated submersions with agitation. After drying, a coating of Viton prepolymer is applied in the fashion described in example 1. The coating is dried and cured. The process is repeated until 80% of the voids left by the original polyurethane foam are filled.

Example 6: Process for Making Exemplary Final Construct with Polyelectrolytic Complexation This example provides a method of forming a construct that includes a process of removing at least part of the matrix. In the sixth example, a polyurethane foam dissolvable in DMSO at 40 C over 3 hours is impregnated with a chitosan (76% deacetylated) solution comprised of 2 parts chitosan, 2 parts acetic acid, and 96 parts deionized water by weight. The impregnation process is done by decanting a solution in a curtain over a moving sheet of the polyurethane foam followed by a continuous compression to 10% of the original height by squeegee rolls, drying using fan blades at 300 PSI using hot air (5% humidity, 60 C). The coated foam is then curtain coated in an alginate solution (2 parts alginate, 98 parts deionized water), curtain washed with deionized water, and dried by fan blades at 300 PSI using hot air (10% humidity, 40 C). The process is repeated until 120% weight pickup (of the original polyurethane foam weight) is attained on a dry basis. The resulting material is neutralized by a wash of 5 molar ammonia in 50/50 ethanol/water, washed with DI water until full neutrality and dried at 40 C for 4 hours. After drying the base polyurethane foam is dissolved in DMSO at 40 C for 4 hours and the material washed in water with agitation for 12 hours.

Example 7: Final Construct

This example provides a method of forming a construct that includes a process of removing at least part of the matrix. In the seventh example, a final construct that is attained by using a dissolvable foam, and a silicone HTV pre-polymer is described. The final construct has a porosity of 86%, average pore size of 650 um with a standard deviation of pore size of 150 um, average interconnection diameter of 350 um with a standard deviation of interconnection diameters of 80 um, average number of interconnections per pore of 6 with a standard deviation of interconnections per pore of 1.4 and an average strut diameter of 155 um with a standard deviation of strut diameters of 37 um.

Example 8: Reinforced Final Construct

This example provides a method of forming a construct that includes a process of removing at least part of the matrix. In the eighth example, a set of reinforced final constructs is described. The constructs are attained using impregnation of dissolvable polyurethane foam, followed by removal of excess solution, drying of the excess solution, repetition of steps to achieve sufficient buildup to afford the construct mechanical integrity in the absence of the polyurethane foam, dissolution of the polyurethane foam and thereafter a sequence of repeat coatings of the original material used during impregnation to achieve filling of the voids left by the dissolvable polyurethane foam. The following constructs are attained:

| Construct # | 1 | 2 | 3 | 4 | 5 |
| --- | --- | --- | --- | --- | --- |
| Porosity | 96% | 94% | 92% | 88% | 82% |
| Avg Pore Diameter (um) | 740 | 730 | 710 | 680 | 640 |
| Average Interconnection Diameter (um) | 450 | 440 | 420 | 390 | 350 |
| Average # of Interconnections/Pore | 7.5 | 7.5 | 7.3 | 7.2 | 7.0 |
| Average Strut Diameter Measured at Minimum (um) | 60 um | 65 um | 75 um | 90 um | 110 um |
| Average % of void space left by the original polyurethane foam | 100% | 90% | 60% | 30% | 5% |

Example 9: Process for Making Final Construct from Hydrogel Composition

In the ninth example a polyurethane foam template having 97.8% porosity, an average pore diameter of 800 um, an average number of interconnections per pore of 9, and an average interconnection diameter of 400 um, is coated with a hydrogel mixture containing 0.1% ethyleneglycol dimethacrylate crosslinker, 0.1% AIBN (azoisobutyronitrile) initiator, and 99.8% 2-hydroxyethyl-methacrylate hydrophilic monomer. The mixture is applied to a 30 cm by 30 cm sheet of polyurethane foam with a thickness of 10 mm. The foam is squeezed by a set of rollers to a thickness of 15% during the decanting to allow maximum impregnation of the mixture, and then again to 25% of original thickness to remove the excess mixture, repeatedly until the pickup by weight is 10% of the original polyurethane foam. The impregnated foam is then placed in a forced air oven at 80 C for 12 hours. The impregnated foam is then submerged in NMP at 40 C for 4 hours, and subsequently washed with DI water at 100 C for 3 hours with agitation. The dissolution and washing process is repeated 3 times. The final construct is soaked in water for 4 hours, blotted dry, and weighed. The measured equilibrium water is 38%.

It is understood that the various embodiments listed in the section above are examples only and can be applied in any combination with each other, or in combination with other embodiments known in the art. Materials, chemical and physical properties, as well as descriptions of microstructure are described as examples, and are not intended to be limiting to the scope of the inventions herein.

The disclosure that follows relates to exemplary methods of use for any of the open celled or semi-open celled constructs herein in medical applications. The methods that follow do not necessarily require any particular final construct described above. Some aspects of the constructs described herein may be applicable to the exemplary methods of use herein, but the constructs herein may be modified in one or more ways, such as if the modification makes the constructs more desirable for a particular use. More specifically, the disclosure describes uses of a polymeric, polymeric composite, polymer-ceramic composite, polymer-metal composite, polymer-polymer blend, or coated aforementioned material containing a given porosity, a specific interconnectivity of the pores, a specific interconnection diameter, and a specific pore size and pore size polydispersity in implantable and non-implantable medical applications. In some embodiments, the material may be used for or in conjunction with drugs or bioactive agents and/or to deliver drugs or bioactive agents to a given tissue, organ, or body part. The material can exist as a standalone device or as a component within a device assembly.

In some particular embodiments, the materials can be used in direct or non-direct contact with tissue. The materials herein may be used in, for example without limitation, wound contact applications, in tissue augmentation or bulking applications, in reconstructive procedures or for tissue support, in organ transplant applications, in buttressing applications, in hernia repair procedures, in vascular anastomosis procedures, in general surgery procedures, in gynecological applications, in surgical adhesion prevention applications, in wound dressing applications, as treatment for ulcers, as treatment for burns including chemical burns, for bone repair, reconstruction, or augmentation procedures, in dental surgery applications, in tissue fixation or anastomosis applications, in cardiac surgery applications, in endovascular treatment applications, in aortic aneurysm treatment applications, in neurosurgical procedures, and in tendon reconstruction surgery, without limitation.

When used in medical applications, the medical devices are optionally comprised at least in part of a fully open or semi-open cell foam that has at least 80% pores by volume in the foam element, wherein the foam element comprises at least one natural or one synthetic polymer. In some embodiments, the foam may be an element that does not have a fixation element. An example of this is a foam that does not contain an adhesive, and is kept in place over tissue by a separate fixation element, such as a tape, gauze covering, or any other fixation mechanism. Additionally, the foam can be attached to at least one, more preferably several, or continuous fixation elements. The fixation elements herein are generally described as being used to attach or secure medical devices to tissue.

Exemplary methods of use herein include uses of open celled or semi-open celled materials in medical applications. Some particular uses include the use of polymeric, open celled or semi-open celled structures comprised of one or more of polydimethyl siloxane or silicone, polyurethane, polyvinyl alcohol, polyvinylpyrrolidone, poly(2-hydroxyethylmethacrylate), polyester, polyether, poly L-lactide, poly L-lactide-co-glycolide copolymer, chitosan or chitosan-chitin copolymer, dextran, Polyvinylidene fluoride, silicone, flurosilicone, polycaprolactone, PEEK, PET, PTFE, PCTFE, PVC, polyethylene, polystyrene, nylon, phenol-formaldehyde, para-aramid, polychloroprene, polyamide, polyacrylonitrile, polyimide, aromatic polyester, poly-p-phenylene-2,6-benzobisoxazole, polypeptide, polysaccharide, or fatty acid polymers or copolymers.

In some uses, the medical device includes a foam element that may be comprised of at least one polymer, and is most optimally comprised of at most three polymers. The polymers may be biostable or biodegradable. In some embodiments, the polymers that comprise the foam element are synthetic and can be a polymer from a class of polyester, polyamide, polyacrylate, polyacrylamide, polycarbonate, polyethers, polyether-esters, polyanhydrydes, polyphenols, polypeptides, polyimides, polyurethanes, polyureas, polysiloxanes, polyvinyls, copolymers or blends thereof. In other embodiments, the polymer is related to the class of polyester, polyamide, polyacrylate, polyacrylamide, polycarbonate, polyethers, polyether-esters, polyanhydrides, polyphenols, polypeptides, polyimides, polyurethanes, polyureas, polisiloxanes, polyvinyls, copolymers or blends thereof.

In some specific embodiments, at least a part of the foam structure is comprised of a soft silicone, polyurethane, or has a backing that is a felt of Dacron, chitosan, wool, poly glycolide, poly lactide, poly carbonate, poly butyrate, a vinyl based polymer, blends or copolymers thereof. Examples of such foam structures or constructs may be described in more detail above.

In some specific embodiments, at least a part of the finished foam composite structure is comprised of silicone or derivatives thereof in conjunction with polyether- or polyester-based polyurethane, examples of which are described above.

In yet other embodiments, at least a part of the finished foam composite structure is comprised of a hydrophilic coating, silicone or derivatives thereof in conjunction with polyether- or polyester-based polyurethane, examples of which are described herein.

In yet other embodiments, at least a part of the foam structure is comprised of a hydrophilic coating, silicone or derivatives thereof in conjunction with polyether- or polyester-based polyurethane, post-processed with a solvent or solvents not limited to dimethylsulfoxide, N-methylpyrrol-dine, 2-ethanol, acetone, and the like. Treatment of the foam with one or more of these solvents impart softness and low friction to the surface in conjunction with extraction of contaminants from the foam matrix, additional details of which are described above.

In yet other embodiments, linear hydrogel polymer, cross-linked hydrogel polymer, linear silicone hydrogel polymer, and cross-linked silicone hydrogel polymer are used as open celled or semi-open celled structures comprising at least one of the following homopolymer or copolymer systems including any polymer which contains units from one or more hydrophilic silicon-containing monomers and/or mac-romers or one of the following homopolymer or copolymer systems including any polymer which contains units from one or more hydrophilic non-silicon-containing monomers and/or macromers. For example, the polymer may include copolymers with the following copolymerizable compounds: acrylic monomers such as methyl acrylate, ethyl acrylate and acrylic acid; methacrylic monomers such as methyl methacrylate, ethyl methacrylate, 2-hydroxyethyl methacrylate and methacrylic acid; siloxane monomers such as tris(trimethylsiloxy)silylpropyl methacrylate, bis(trimethylsiloxy)methylsilylpropyl methacrylate, pentamethyldisi-loxanepropyl methacrylate, tris(trimethylsiloxy)silylpropyloxyethyl methacrylate, and tris(polydimethylsiloxy)silylpropyl methacrylate; fluorosiloxane monomers such as tri(dimethyltrifluoropropylsiloxy)silylpropyl methacrylate; fluoroalkyl monomers such as 2,2,2-trifluoroethyl methacrylate, 2,2,3,3,3-pentafluoropropyl methacrylate and hexafluoroisopropyl methacrylate; fluoroalkyl and fluoroalkylether monomers containing hydroxyl group such as 1,1,2,2-tetrafluoroethoxy-2-hydroxypropyl methacrylate; hydrophilic monomers such a N-vinylpyrrolidone, N,N'-dime thylacry-lamide and N-vinyl-N-methylacetamide; crosslinkable monomers such as ethylene glycol dimethacrylate, tetraethylene glycol dimethacrylate and tetramethyldisiloxanebis (propylmethacrylate). Among these, copolymers with siloxane methacrylates, fluoroalkylsiloxane methacrylates, fluoroalkyl methacrylates, fluoroalkylether methacrylates containing hydroxyl groups, hydrophilic monomers, cross-linkable monomers with two or more unsaturated groups within a molecule and siloxane macromers with polymer-izable unsaturated groups at molecular ends.

In yet other embodiments, polymer-ceramic composite are used as open celled, or semi-open celled, structures comprising at least one of the following ceramics or ores including aluminium magnesium boride, aluminum oxyni-tride, barium strontium cobalt ferrite, barium titanate, beryllium oxide, bismuth strontium calcium copper oxide, bisque, boron nitride, briquetage, calcium aluminates, crittersol, dysprosium titanate, clay, ferrite, frit, fumed silica, germanium dioxide, glass, hafnium diboride, hydroxylapatite, jes-monite, lanthanum gallium silicate, lanthanum hexaboride, lanthanum strontium cobalt ferrite, lanthanum strontium manganite, lead scandium tantalite, lead zirconate titanate, lithophane, lumicera, magnesium diboride, magnesium oxide, martensite, molybdenum disilicide, nile silt, quartz, silicon carbide, silica, silicon boride, silicon dioxide, silicon nitride, silicon oxynitride, strontium titanate, zirconia, titanium carbide, carbon nanotubes, tungsten disilicide, tungsten nitride, yttrium barium copper oxide, zinc oxide, zirconia toughened alumina, zirconium dioxide, argentite, barite, bauxite, beryl, bornite, cassiterite, chalcocite, chalcopyrite, chromite, cinnabar, cobaltite, columbite-tantalite or coltan, dolomite, galena, hematite, ilmenite, magnetite, malachite, molybdenite, pentlandite, pyrolusite, scheelite, sperrylite, sphalerite, uraninite, wolframite or combination of one or more thereof in the form of a powder, fiber, dendritic structure, flake, conformal or non-conformal coating, additive or blend.

In yet other embodiments, the open or semi-open cell structure can be comprised at least in part of a polymer-metal composite including metals such as lithium, sodium, potassium, rubidium, cesium, francium, beryllium, magnesium, calcium, strontium, barium, radium, aluminum, gallium, indium, tin, thallium, lead, bismuth, scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, ruther-fordium, dubnium, seaborgium, bohrium, hassium, meitne-rium, darmstadtium, roentgenium, copernicium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, lawrencium or an alloy of one or more thereof. In yet other embodiments, at least a part of the open celled structure or a coating on the open celled structure can contain a metalorganic compound such as for example silver sulfadiazine antibiotic.

Additionally, agents comprising drugs, strengthening additives, antimicrobials, disinfectants, wettability enhancers, UV stabilizers, texturizers, and the like may be a component in the material. The component may be chemically bonded to the polymer or can exist as a physical blend or entrapped within the polymer matrix.

In some embodiments herein, a lost matrix approach may be used to generate open celled and semi-open celled structures. The polymer can be cured, dried, or otherwise solidified in the presence of a liquid or solid porogen component comprising a particle, fiber, and the like of a predetermined size and geometry. After solidification of the polymer the liquid or solid porogen component is dissolved or otherwise removed to render a final material that is open celled or semi-open celled.

In yet other methods, a lost template approach can be used to generate open celled and semi-open celled structures. The polymer is cured, dried, or otherwise solidified as a conformal coating around open celled or semi-open celled polyurethane foam as the template, examples of which are described elsewhere herein. After solidification of the polymer the polyurethane foam template optionally may be at least partially dissolved or at least partially removed to render a final material that is open celled or semi-open celled. The polyurethane foam template may, however, not be removed.

In yet other methods, a template approach can be used to generate open celled and semi-open celled structures. The polymer can be cured, dried, or otherwise solidified as a conformal coating around open celled or semi-open celled polyurethane foam as the template. The construct can be used as-is as the medical device, post-processed with solvents and then used as-is as the medical device, or coated with a polymeric substance having hydrophilic properties to promote wettability to bodily fluids (examples of which are described herein) and then used as-is.

Figure 4:
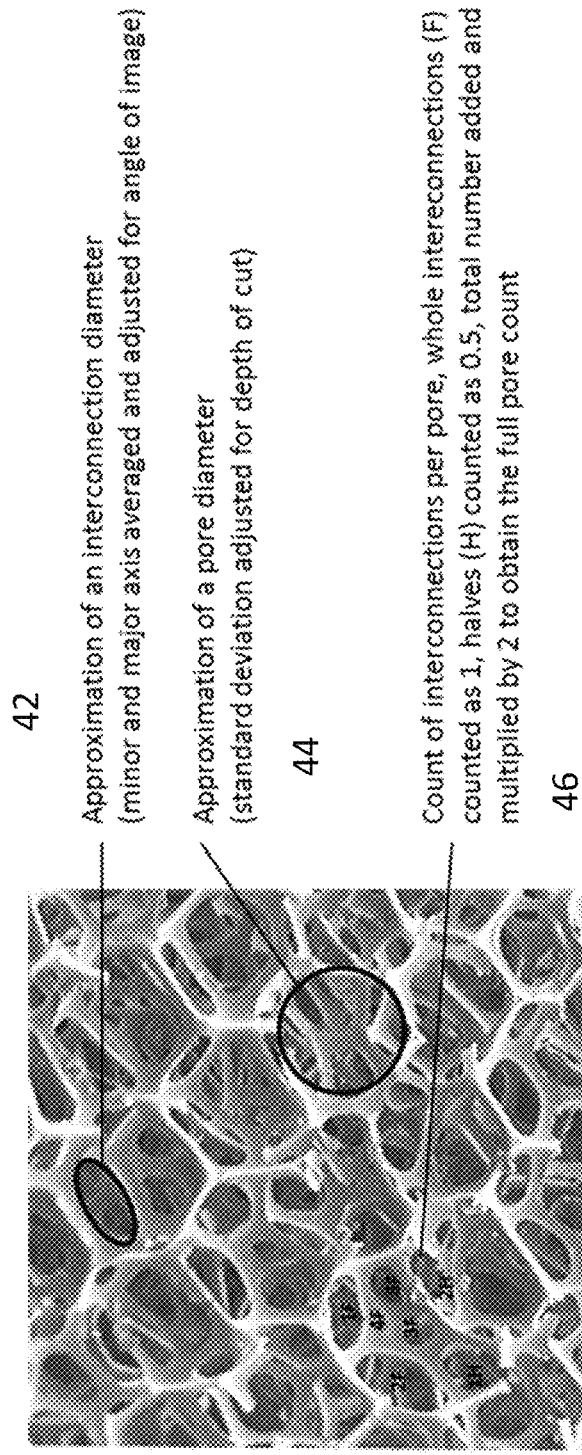
FIG. 4 illustrates scanning electron micrograph image of features within an open cell material.

FIGS. 3A-3C show scanning electron micrograph images of celled materials for comparison. Fully open cell material (FIG. 3A) has interconnections between all pores as shown, semi-open cell material (FIG. 3B) contains some closed pores which do not interconnect with neighboring pores as shown, and fully closed cell material (FIG. 3C) has all pores as closed cell as shown. In FIG. 4, interconnection diameter 42, pore diameter 44, and count of interconnected pores 46 are features that can help describe the structure of the constructs herein.

In any of the examples herein, the final construct may have a porosity of 40-99.7%, in more particular embodiments, the porosity is 60-99%, and in some most particular embodiments, the porosity is 75-97%. Exemplary benefits of highly porous constructs are described herein. In addition, the material shall contain pores having one or more interconnections per pore. More specifically, the number of interconnections per pore can average between 2.1 and 16, and more specifically between 2.5 and 12. The interconnection diameter can range on average from 5 um-1400 um, in a more particular specific embodiment from 20 um-1200 um, and most particular from 50-900 um. The material can contain a pore size averaging between 20 and 2400 um, and more specifically between 50-1800 um containing a standard deviation of pore sizes ranging from 5-2500 um, and more specifically from 50-1500 um.

In general, materials herein to be used for medical applications including surgical, outpatient procedures, homecare, and self-care, as well as in-patient, emergency room and operating room in both implantable and non-implantable medical procedures.

In some exemplary uses, the material may be used in conjunction with drugs, biologics, or other bioactive agents administered at the time of use, impregnated prior to or during use, coated with a drug, biologic, or bioactive agent, or a coating containing a drug, biologic, or a bioactive agent for controlled or immediate release into the surrounding environment. The specific agents may include small molecule drugs, peptides, DNA, RNA, proteins, antibodies, enzymes, sugars, fatty acids or other bioactive, biologic, or biologically derived molecules.

In some uses, the open celled or semi-open celled material can be used to deliver said drugs, bioactive agents, or biologics to a given tissue, organ, or body part including without limitation release of said agents to the skin, dermis, epidermis, sub cutis, muscle tissue, vascular tissue, nerve tissue, fluid filled spaces and cavities inside the body, parts of the gastrointestinal tract, cardiovascular tissue, bone and bone marrow, tendons and ligaments, tissue membranes, kidneys, liver, pancreas, lungs, glands, fatty tissue, eye, or oral cavity.

More specifically, in some embodiments, the materials can be used in wound care applications, for treatment of burns, chronic or non-chronic ulcers, skin infections, gunshot wounds, scar reduction post cosmetic or therapeutic surgery, or for general protection of or drug delivery to the skin. In other embodiments, the materials can be used in tissue augmentation or bulking applications, such as support or general augmentation of tissue during a breast reconstruction or augmentation procedure, post-tumor removal tissue filling, post-surgical tissue removal local tissue augmentation, in reconstructive procedures or for tissue support, in organ transplant applications to both support the transplant, deliver drugs or bioactive agents to the transplant, and to protect the transplant prior to, during, and after transplantation, in buttressing applications to support suturing, anastomosis, or general tissue connection procedures, in hernia repair procedures as support, prevention of formation of tissue adhesions, prevention of infection or tissue erosion, in vascular anastomosis procedures as support, drug delivery to the vascular tissue to prevent restenosis and infection after surgery or during post-surgical access, as support to enhance through direct activity or drug delivery formation of tissue to support the anastomosis, in general surgery procedures to reduce infection or reduce surgical adhesions, in gynecological applications as tissue support, augmentation, prevention of infection, in general surgical adhesion prevention applications for surgeries in the abdomen, near tendons, ligaments, muscles, intensities, in wound dressing applications to protect the wound, prevent infection or enhance healing, as treatment for ulcers to promote and enhance healing or potentially deliver bioactive agents to the ulcer, as treatment for burns including chemical burns to reduce scaring, enhance appearance of the burn post treatment, prevent infection, reduce pain, promote healing, for bone repair, reconstruction, or augmentation procedures to enhance the strength of the repaired, reconstructed, or augmented segment, to prevent infection, to form the shape of the bone with the use of demineralized bone, bone morphogenic protein, or bone cement, to enhance healing and provide support, in dental surgery applications to promote healing, prevent infection or for generally forming a tissue scaffold for tissue ingrowth, overgrowth, or general promotion of a formation of one or more given tissue types, in tissue fixation or anastomosis applications as support and means for local drug delivery, in cardiac surgery applications to deliver drug to affected tissue or post-op to the surgical site, during treatment of aortic aneurysms, berry aneurisms, fusiform aneurysms, or vascular malformations for blocking of cavities, support of normal tissue architecture restoration, promotion of tissue growth within a region, filling, pressure reduction, or prevention of rupture. Additionally, the material can be used in neurosurgical procedures to enhance tissue regeneration or denovo tissue formation post excision as well as in treatment of tendon and ligament reconstruction to enhance the healing rate, strengthen the reconstructed tissue, or support during growth.

In other specific aspects, the material can be used during cancer excision procedures to locally deliver therapeutics for one or more of, without limitation, prevention of infection reduction of tumor growth, promotion of tumor necrosis and apoptosis, tissue bulking, tissue support, and delivery of bioactive agents locally to the tissue.

It should be understood that the formulation, materials, methods of use, microstructures, or bioactive agents may be varied by one skilled in the art, to the extent that the structures described here within perform the desired function and remain within the scope of the present inventions. Various parts, components or characteristics may be used in combination, with or without modification by someone skilled in the art to achieve the desired functionality of the aforementioned formulation.

Moreover, all individual features and methods of use described herein, and each and every combination of two or more of such features and methods of use, are included within the scope of the present inventions provided that these features and methods of use in such a combination are not mutually inconsistent. It is understood that certain portions or combinations of such portions can be varied by someone trained in the art while still achieving the goals of the disclosure.

Finally, it is understood that the specific ranges provided in the current disclosure are not restrictive and are for example purposes only, values outside of the specified ranges may be used to achieve the benefits provided herein without modification to the proposed mechanistic principals.

Exemplary Constructs and Methods of Use

Example 10

In an example of a reconstructive procedure after a partial or complete mastectomy of the breast is performed with a direct implantation of a textured breast implant. The tissue surrounding the implant is augmented with a 15×5 cm sheet of 4.5 mm thick silicone foam containing 87% porosity, 560 um average pore diameter, 350 um average interconnection diameter, and 5.4 interconnections per pore. The silicone matrix allows for tissue disorganization, preventing the formation of an organized foreign body capsule around the implant and thereby reducing the chance of post-surgical capsular contracture or general tissue stiffness. Additionally the foam provides bulk to the surrounding of the implant thereby augmenting the support for the implant in the surrounding tissue.

Example 11

In a variation of Example 10, the foam is comprised of biodegradable collagen and is attached to the implant containing 93% porosity, 740 um average pore size, 540 um average interconnection diameter, and 7.4 interconnections per pore on average throughout the foam.

Example 12

A 2.5 cm wide 5 cm long strip of fully open celled chitosan foam (99.7% deacetylated), containing 10% by weight absorptive hydrogel polymer, and attached to two sheets used for fixation to healthy tissues at either side (4 cm wide and 5 cm long each) is used for wound healing post hemostasis. Fixation sheets contain a pressure sensitive adhesive, and are bound to each other at the edges by two elastomeric strips. Once the backing is removed and the device is applied to the wound, the pressure sensitive adhesive attaches itself to healthy tissues surrounding the wound site, and the elastomeric strips apply contraction to the wound site by pulling the fixation sheets together. The fully open celled chitosan foam promotes tissue healing by antibacterial and progranulative properties, while the hydrogel removes exudate. The remaining open cells allow for sufficient oxygen permeability to give an optimal chemical environment while offering protection from infection and mechanical stresses.

Example 13

A bioactive agent moderating one or more stages of inflammation or proliferation is delivered to the wound site through release from the construct in example one and optionally using a permeation agent such as dimethyl sulfoxide. For the purpose of this specific example an Anti-HMGB1 antibody is delivered to the wound site to attenuate vascular hyperpermeability and promote the wound healing process.

Example 14

In an example, a wound dressing that is designed to be applied during the hemostasis stages of wound healing contains collagen, chitosan, and optionally alginate microparticles at the wound contacting surface, as well as one or more growth factors intended to initiate earlier onset of the granulation and proliferation stages of wound healing. The materials are absorbed and separated from the top layer of the construct, which is comprised of a silicone foam, with 95% open cells, containing absorptive hydrogel embedded in approximately 30% of the open cells and optionally containing a bioactive agent to promote tissue formation during the later stages of wound healing.

Example 15

A wound dressing that is applied during an early stage of wound healing that is equipped with an element designed to shield the wound from stresses due to deformation of surrounding tissues has a restraining element that is designed to allow the functionality of the shielding element to be used only after the hemostatic stage of wound healing has been completed. The restraining element in this example is an exoskeletal frame that maximally prevents the deformation of the wound dressing, and the shielding element in this example are a set of contracting strips that pull the wound dressing in a contractile direction perpendicular to the wound edge.

Example 16

A foam-based medical device is placed over a wound during an early stage of wound healing. The construction of the foam device is a polyurethane foam having greater than 75% open cell coated with medical grade silicone having a shore A durometer of 30. The foam construct is post-processed by immersion in dimethylsulfoxide at 60 degrees C. for one hour followed by washings of water and ethanol. The resulting foam is porous, soft and pliable, and conforms to anatomical features when in use to support wound healing procedures.

Example 17

A modification of the device described in EXAMPLE 15 whereby a hydrophilic coating having an equilibrium water content of 35-85% with a dried thickness of 5-50 microns is applied to the surface of the silicone coating. The resulting foam is wettable to water and is soft and pliable and conforms to anatomical features to support wound healing.

Example 18

The wound dressing is equipped with two sets of shielding elements that pull on the wound dressing with different tension during different stages of wound healing allowing for optimal tension levels during the proliferative and granulation stages of wound healing respectively. The first stage is activated upon placement of the wound dressing as the shielding elements are exposed immediately post binding of the adhesive elements to the healthy tissues, the second stage is optionally activated during a later stage of wound healing allowing for optimization of tension at the wound site.

Example 19

A 100% silicone foam having greater than 95% open cells with skin-free open cell porous surfaces having a range of thicknesses between 0.1 mm and 25 mm serves as a wound dressing. The length and width of the wound dressing is determined by the size and geometry of the wound and the preference by the administering party. The foam is applied over the early or late stage wound and is in direct contact with the skin or skin surface. The silicone foam is fixed and kept into position by use of tape, an adhesive gauze, gauze with tape, or any other common fixation methods. The silicone foam is exchanged with a new foam at 2 days, 3 days, or 7 days.

Example 20

Reference is made to Example 19 with the following difference. The silicone foam contains a fixation element on one side in the form of a repositionable adhesive. Fixation using a secondary device such as tape is not needed.

Example 21

A 100% silicone foam having greater than 95% open cells with skin-free open cell porous surfaces having a range of thicknesses between 0.1 mm and 25 mm serves as a scar reduction patch. The length and width of the patch is determined by the size and geometry of the wound and the preference by the administrating party. The foam is applied over the scar following surgery or after some initial wound healing after a surgical procedure or trauma and is in direct contact with the skin. The silicone foam contains a repositionable adhesive on one side and is what is used for fixation onto the skin.

Example 22

A composite open cell foam having silicone as the base component coated with a hydrogel composition serves as a wound dressing. The hydrogel composition is a cross-linked hydrogel having an equilibrium water content between 30-99%. The hydrogel coating is conformal with regards to the open cell interconnected network of the silicone base. The wound dressing can be applied to the skin surface in the xerogel state meaning that the foam composite is dry. Alternatively, the wound dressing can be applied to the skin surface in the hydrated state. The open cell composite device is very effective in withdrawing exudate from the wound area.

Example 23

Reference is made to Example 14, with the following difference. The hydrogel composition contains an anti-microbial agent such as nanosilver, biguanide, or other bacteriostatic or bactericidal agent.

Example 24

A foam made with a bioresorbable, biocompatible, and hypoallergenic polymer is implanted in a surgical site subcutaneously prior to the closure of the tissue to serve as a tissue augmentation matrix to prevent a recessed appearance of the wound bed post-surgical excision such as in the case of melanoma in-situ treatment, or removal of atypical nevus. The matrix is comprised of a hydrophilic, highly porous >80% plus porosity, highly interconnected >3.4 interconnections per pore, large pore diameter average >150 um, and a large pore interconnection diameter structure >75 um on average. The material is partially crosslinked hyaluronic acid with star-peg crosslinking agents and is modified with bioactive agents to promote wound healing that are eluted into the wound bed over a 7 day time period. The device is fixated by round tabs spaced out at intervals of approximately 25% of the material dimensions (length and width in case of a rectangular sheet and diameter in case of a circular disk).

Example 25

The material is a wound dressing of 0.5×0.5 cm in diameter up to a sheet of 25×25 cm in length and width and serves as a wound dressing or drainage sheet for chronic ulcers. The material has a silicone sheet and a hydrophilic foam attached to the silicone sheet. The silicone sheet is 100-250 um in thickness and the hydrophilic interconnected foam is 2.5 mm in thickness. The porosity of the foam is >75%, the interconnectivity is in excess of 2.3 interconnections per ore and the pore interconnection diameter is on average 180 um (while the pore diameter is on average 250 um). The hydrophilic polymer may absorb moisture to 24-180% mass/mass and can contain antimicrobial agents that are either released into the foam or into the foam and into the top layer of the granulation tissue as the wound is occluding.

Example 26

Three 25×10 cm sheets of open celled poly gamma hydroxy butyrate foam containing 94% porosity, 840 um average diameter pores, 620 um average interconnection diameter, and 8.7 interconnections per pore is implanted in conjunction with a liver transplant, positioned on 120 degree axis from three sides of the transplant. The polymeric foam contains anti-rejection drugs for controlled release over 2 years post implantation. The medication is released locally, to the targeted tissues, and reduces the chance of early rejection or an immunogenic response. Additionally, side effects from systemic administrations are minimized as the treatment is conducted locally. Finally, a fibrous capsule response is prevented as the tissue surrounding the transplant is disorganized allowing for a more natural tissue architecture to form around the transplant.

Example 27

A 5×5 cm 2.5 mm thick semi-open celled foam is implanted as a cardiac support mesh during open heart surgery, the foam, comprised of Dacron, contains 98.1% porosity, an average pore size of 350 um, and an average interconnection diameter of 150 um. The foam also contains an average number of interconnections per pore of 4.3. The implanted material allows for tissue ingrowth and provides support during suturing and post-surgery. The material is used for fixation and to deliver antithrombotic and pro-healing agents locally to the tissue, minimizing the risk of post-surgical adverse events. The material is fixated to the surrounding tissue with sutures and is non-biodegradable being overgrown and integrated into the surrounding tissues over a period of 3-6 months.

Example 29

A 5×3 cm 3 mm thick sheet of open celled chitosan foam, containing an average pore size of 650 um, an average interconnection diameter of 350 um, an average number of interconnections per pore of 6.3, and an average porosity of 94% is used to support an arteriovenous fistula during an anastomosis for dialysis access. The open celled foam is 87% deacetylated chitosan of medium molecular weight and is coated with a 76% deacetylated chitosan embedded with a pro-proliferative agent. The pro-proliferative agent is delivered to the arteriovenous fistula over the first 4 weeks, with a burst release over the first 3 days and promotes fistula maturation, while the chitosan reduced the risk of infection due to access of the fistula for dialysis. In this example a dual purpose is served by the foam, to bulk the anastomosis promoting the generation of a supportive structure for access (or increased time to access) and prevention of infection through controlled drug delivery.

What is claimed is:

1. A method of making a biocompatible open or semi-open celled construct for medical applications, the method comprising:
submerging an open or semi-open celled polyurethane foam template into a silicone dispersion to expose the polyurethane foam template to the silicone dispersion, the polyurethane foam template comprising a plurality of template struts that define a plurality of template pores,
allowing the silicone to pass into the plurality of template pores;
removing at least some of the silicone dispersion from the plurality of template pores;
forming a construct that includes a plurality of construct struts that define a plurality of construct pores, wherein forming the construct comprises curing the silicone to form a conformal silicone coating on the plurality of template struts,
the plurality of construct struts having a thickness from 30 microns to 90 microns,
the conformal silicone coating having a thickness from 1 micron to 20 microns, and
wherein the construct is 80-98% open pore.

2. The method of claim 1, wherein forming the construct further comprises, at a time subsequent to the curing step, forming a hydrophilic layer on the conformal silicone coating to impart wettability.

3. The method of claim 1, wherein the dispersion is at most 35% silicone.

4. The method of claim 1, wherein the construct, in an image of a top or a bottom of the construct, has an open area %, defined as open space between the plurality of construct struts, and wherein the polyurethane template in the absence of the conformal silicone coating, in an image of a top or a bottom of the polyurethane template, has an open area %, defined as open space between the plurality of template struts, and wherein the difference between the construct open area % and the template open area % is less than 10%.

5. The method of claim 4, wherein the difference between the construct open area % and the template open area % is less than 5%.

6. The method of claim 1, further comprising, at a time subsequent to curing the silicone, performing an extraction to remove uncured silicone.

7. The method of claim 1, wherein the plurality of construct pores have a diameter from 200 to 600 microns.

8. The method of claim 1, wherein the plurality of construct pores have an interconnection diameter from 5-2200 microns.

9. The method of claim 1, wherein removing at least some of the silicone dispersion from the plurality of template pores comprises spinning the polyurethane foam template to remove at least some of the silicone dispersion.

10. The method of claim 1, further comprising repeating the submerging, allowing, removing, and curing steps.

11. The method of claim 10, wherein repeating the steps comprises repeating the submerging, allowing, removing, and curing steps from 1-10 times.

12. The method of claim 11, wherein repeating the steps comprises repeating the submerging, allowing, removing, and curing steps from 1-5 times.

13. The method of claim 12, wherein repeating the steps comprises repeating the submerging, allowing, removing, and curing steps from 1-3 times.

14. The method of claim 1, further comprising exposing the plurality of construct struts to DMSO.

15. The method of claim 14, wherein exposing the plurality of construct struts to DMSO comprises exposing the plurality of construct struts to DMSO for at least 30 minutes.

16. The method of claim 15, further comprising performing a step to extract the DMSO.

17. The method of claim 2, wherein forming the hydrophilic layer on the conformal silicone coating comprises forming the hydrophilic layer that has a thickness of less than 5 microns.

18. The method of claim 2, further comprising, prior to forming the hydrophilic layer, corona treating the conformal silicone coating and exposing the corona treated conformal silicone coating to a coupling agent.

19. The method of claim 18, wherein the coupling agent is a silane coupling agent.

* * * * *